(12) United States Patent
Bateman et al.

(10) Patent No.: US 10,830,775 B2
(45) Date of Patent: Nov. 10, 2020

(54) TAU KINETIC MEASUREMENTS

(71) Applicant: Washington University, St. Louis, MO (US)

(72) Inventors: Randall Bateman, St. Louis, MO (US); Chihiro Sato, St. Louis, MO (US); Kwasi Mawuenyega, St. Louis, MO (US); Tim Miller, St. Louis, MO (US); David Holtzman, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/515,909

(22) PCT Filed: Sep. 30, 2015

(86) PCT No.: PCT/US2015/053283
§ 371 (c)(1),
(2) Date: Mar. 30, 2017

(87) PCT Pub. No.: WO2016/054247
PCT Pub. Date: Apr. 7, 2016

(65) Prior Publication Data
US 2017/0307639 A1    Oct. 26, 2017

Related U.S. Application Data

(60) Provisional application No. 62/057,853, filed on Sep. 30, 2014.

(51) Int. Cl.
*G01N 33/68* (2006.01)
*G01N 33/58* (2006.01)
*A61K 51/08* (2006.01)
*A61K 39/00* (2006.01)

(52) U.S. Cl.
CPC ......... *G01N 33/6896* (2013.01); *A61K 51/08* (2013.01); *G01N 33/58* (2013.01); *A61K 2039/505* (2013.01)

(58) Field of Classification Search
CPC .... G01N 33/6896; G01N 33/58; A61K 51/08; A61K 2039/505
See application file for complete search history.

(56) References Cited

U.S. PATENT DOCUMENTS

| | | |
|---|---|---|
| 5,767,248 A | 6/1998 | Roses et al. |
| 6,320,024 B1 | 11/2001 | Roberts |
| 7,070,941 B2 | 7/2006 | Zhao et al. |

(Continued)

FOREIGN PATENT DOCUMENTS

| | | |
|---|---|---|
| EP | 1886112 B1 | 7/2014 |
| EP | 3066979 A1 | 9/2016 |

(Continued)

OTHER PUBLICATIONS

Iqbal et al. Tau in Alzheimer disease and related tauopathies. Curr Alzheimer Res. Dec. 2010;7(8):656-64.*

(Continued)

*Primary Examiner* — Gregory S Emch
(74) *Attorney, Agent, or Firm* — Polsinelli PC

(57) ABSTRACT

The invention relates to in vitro methods for measuring the in vivo metabolism of tau in a subject.

19 Claims, 18 Drawing Sheets
(12 of 18 Drawing Sheet(s) Filed in Color)
Specification includes a Sequence Listing.

(56) References Cited

U.S. PATENT DOCUMENTS

| | | |
|---|---|---|
| 7,442,516 B2 | 10/2008 | Ohno et al. |
| 7,816,083 B2 | 10/2010 | Grupe et al. |
| 7,829,291 B2 | 11/2010 | Caprioli |
| 7,892,845 B2 | 2/2011 | Bateman et al. |
| 8,232,107 B2 | 7/2012 | Bateman et al. |
| 2003/0228259 A1 | 12/2003 | Hellerstein |
| 2004/0157267 A1 | 8/2004 | Huang et al. |
| 2004/0224336 A1 | 11/2004 | Wagner |
| 2004/0248197 A1 | 12/2004 | Holtzman et al. |
| 2005/0019251 A1 | 1/2005 | Hellerstein |
| 2005/0224710 A1 | 10/2005 | Matsuo et al. |
| 2006/0020440 A1 | 1/2006 | Hellerstein |
| 2007/0160585 A1 | 7/2007 | Fujinaga et al. |
| 2007/0231909 A1 | 10/2007 | Hunter |
| 2007/0264631 A1 | 11/2007 | Suematsu et al. |
| 2008/0003570 A1 | 1/2008 | Rogers et al. |
| 2008/0131893 A1 | 6/2008 | Maraganore et al. |
| 2008/0132685 A1 | 6/2008 | Chakrabartty et al. |
| 2008/0145941 A1 | 6/2008 | Bateman et al. |
| 2009/0035298 A1 | 2/2009 | Holtzman et al. |
| 2009/0041661 A1 | 2/2009 | Hellerstein |
| 2009/0074763 A1 | 3/2009 | Padhi et al. |
| 2009/0142766 A1 | 6/2009 | Holtzman et al. |
| 2009/0202432 A1 | 8/2009 | Schenk et al. |
| 2009/0264355 A1 | 10/2009 | Holtzman et al. |
| 2010/0111852 A1 | 5/2010 | Yoshida |
| 2010/0316564 A1 | 12/2010 | Sigurdsson et al. |
| 2011/0111511 A1 | 5/2011 | Bateman et al. |
| 2011/0166035 A1 | 7/2011 | Kleinschmidt et al. |
| 2011/0177509 A1 | 7/2011 | Holtzman et al. |
| 2011/0294138 A1 | 12/2011 | Bateman et al. |
| 2012/0015371 A1 | 1/2012 | West et al. |
| 2012/0282642 A1 | 11/2012 | Bateman et al. |
| 2013/0115716 A1 | 5/2013 | Bateman et al. |
| 2014/0199718 A1 | 7/2014 | Bateman et al. |
| 2014/0302520 A1 | 10/2014 | Bateman et al. |
| 2014/0370619 A1 | 12/2014 | Holtzman et al. |
| 2015/0140672 A1 | 5/2015 | Bateman et al. |
| 2015/0254421 A1 | 9/2015 | Bateman et al. |
| 2016/0139142 A1 | 5/2016 | Bateman et al. |
| 2016/0169916 A1 | 6/2016 | Holtzman et al. |
| 2016/0178646 A1 | 6/2016 | Bateman et al. |
| 2016/0195550 A1 | 7/2016 | Bateman et al. |
| 2017/0137502 A1 | 5/2017 | Pfeifer et al. |
| 2017/0146557 A1 | 5/2017 | Bateman et al. |
| 2017/0260263 A1 | 9/2017 | Nov k et al. |

FOREIGN PATENT DOCUMENTS

| | | |
|---|---|---|
| WO | 1999017765 A1 | 4/1999 |
| WO | 2003061479 A1 | 7/2003 |
| WO | 2003068919 A2 | 8/2003 |
| WO | 2004018997 A2 | 3/2004 |
| WO | 2005081943 A2 | 9/2005 |
| WO | 2006017812 A1 | 2/2006 |
| WO | 2006081008 A2 | 8/2006 |
| WO | 2006107814 A3 | 10/2006 |
| WO | 2007047323 A2 | 4/2007 |
| WO | 2007106762 A2 | 9/2007 |
| WO | 2009062152 A1 | 5/2009 |
| WO | 2009076581 A1 | 6/2009 |
| WO | 2010011506 A2 | 1/2010 |
| WO | 2010056815 A1 | 5/2010 |
| WO | 2010065878 A1 | 6/2010 |
| WO | 2011149947 A2 | 12/2011 |
| WO | 2012045882 A2 | 4/2012 |
| WO | 2012075422 A2 | 6/2012 |
| WO | 2012106363 A2 | 8/2012 |
| WO | 2012140296 A1 | 10/2012 |
| WO | 2013081735 A1 | 6/2013 |
| WO | 2013082307 A1 | 6/2013 |
| WO | 2013096451 A2 | 6/2013 |
| WO | 2014008404 A1 | 1/2014 |
| WO | 2014081851 A1 | 5/2014 |
| WO | 2014161890 A1 | 10/2014 |
| WO | 2016054247 A1 | 4/2016 |
| WO | 2017053739 A1 | 3/2017 |
| WO | 2019213612 A1 | 11/2019 |

OTHER PUBLICATIONS

Yanamandra et al. Anti-tau antibodies that block tau aggregate seeding in vitro markedly decrease pathology and improve cognition in vivo. Neuron. Oct. 16, 2013;80(2):402-414. doi: 10.1016/j.neuron.2013.07.046. Epub Sep. 26, 2013.*

Yamada et al. Neuronal activity regulates extracellular tau in vivo. J Exp Med. Mar. 10, 2014;211(3):387-93. doi: 10.1084/jem.20131685. Epub Feb. 17, 2014.*

Hart, M. et al., "Beta-Amyloid Protein of Alzheimer's Disease Is Found in Cerebral and Spinal Cord Vascular Malformations," Am. J. Pathol., Jul. 1988, pp. 167-172, vol. 132, No. 1.

Hasten, D. et al., "Isolation of human skeletal muscle myosin heavy chain and actin for measurement of fractional synthesis rates," Am. Physiol. Soc., 1998, pp. E1092-E1099, vol. 275.

Hasten, D. et al., "Resistance exercise acutely increases MHC and mixed muscle protein synthesis rates in 78-84 and 23-32 yr olds," Am. J. Physiol. Endocrinol. Metab., 2000, pp. E620-E626, vol. 278.

Hebert, L. et al., "Annual Incidence of Alzheimer Disease in the United States Projected to the Years 2000 through 2050," Alzheimer Disease and Associated Disorders, 2001, pp. 169-173, vol. 15, No. 4.

Henriques, A. et al., "Isoform Specific Amyloid-beta Protein Precursor Metabolism," J. Alzheimer's Disease, Mar. 2007, pp. 85-95, vol. 11, No. 1.

Holtzman, D. et al., "Acid Urea Polyacrylamide Gel Electrophoresis: A Completely Denaturing Protocol for the Identification of Multiple Abeta Peptides Within a Single Lane," Society for Neuroscience, 2002, 1 pg. (Abstract Only).

Holtzman, D. et al., "Apolipoprotein E Facilitates Neuritic and Cerebrovascular Plaque Formation in an Alzheimer's Disease Model," Ann. Neurol., Jun. 2000, pp. 739-747, vol. 47, No. 6.

Holtzman, D. et al., "Apolipoprotein E isoform-dependent amyloid deposition and neuritic degeneration in a mouse model of Alzheimer's disease," PNAS, Mar. 14, 2000, pp. 2892-2897, vol. 97, No. 6.

Houle, P. et al., "Pump-regulated Lumbar Subarachnoid Drainage," Neurosurgery, Apr. 2000, pp. 929-932, vol. 46, No. 4.

International Search Report and Written Opinion dated Aug. 1, 2008 from related International Patent Application No. PCT/US2006/012200; 5 pgs.

International Search Report and Written Opinion dated May 8, 2007 from related International Patent Application No. PCT/US2006/039766; 6 pgs.

International Search Report and Written Opinion dated Feb. 13, 2009 from related International Patent Application No. PCT/US2008/82985; 7 pgs.

International Search Report and Written Opinion dated Feb. 20, 2009 from related International Patent Application No. PCT/US2008/086529; 8 pgs.

International Search Report and Written Opinion dated Dec. 28, 2009 from related International Patent Application No. PCT/US2009/050255; 14 pgs.

International Search Report and Written Opinion dated Jan. 13, 2010 from related International Patent Application No. PCT/US2009/064146; 8 pgs.

International Search Report and Written Opinion dated Nov. 23, 2011 from related International Patent Application No. PCT/US2011/037754; 8 pgs.

International Search Report and Written Opinion dated Jul. 27, 2012 from related International Patent Application No. PCT/US2011/063121; 12 pgs.

International Search Report and Written Opinion dated Mar. 14, 2013 from related International Patent Application No. PCT/US2012/060597; 12 pgs.

International Search Report and Written Opinion dated Feb. 22, 2013 from related International Patent Application No. PCT/US2012/070623; 9 pgs.

(56) References Cited

OTHER PUBLICATIONS

International Search Report and Written Opinion dated Oct. 14, 2013 from related International Patent Application No. PCT/US2013/049333; 17 pgs.
International Search Report and Written Opinion dated Feb. 11, 2014 from related International Patent Application No. PCT/US2013/071042; 14 pgs.
International Search Report and Written Opinion dated Aug. 29, 2014 from related International Patent Application No. PCT/US2014/031602; 11 pgs.
International Search Report and Written Opinion dated Jan. 22, 2016 from related International Patent Application No. PCT/US2015/053283; 10 pgs.
Israelson, A. et al, "Misfolded Mutant SOD1 Directly Inhibits VDAC1 Conductance in a Mouse Model of Inherited ALS," Neuron, Aug. 26, 2010, pp. 575-587, vol. 67, No. 4.
Jerzy, L. et al., "Total tau in cerebrospinal fluid differentiates Alzheimer's disease from vascular dementia," Intnl. Med. J. Exper. Clin. Res., Nov. 2003, pp. CR484-CR488, vol. 9, No. 11 (PubMed ID: 14586274 abstract only).
Kar, S. et al., "Interactions between beta-amyloid and central cholinergic neurons: Implications for Alzheimer's disease," J. Psych. Neurosci., Jan. 1, 2004, pp. 427-441, vol. 29, No. 6.
Keeney, A. et al., "Differential Effects of Acute and Chronic Social Defeat Stress on Hypothalamic-Pituitary-Adrenal Axis Function and Hippocampal Serotonin Release in Mice," J. Neuroendroain., 2006, pp. 330-338, vol. 18, Blackwell Publishing.
Kennedy, J. et al., "Preferential Cerebrospinal Fluid Acetylcholinesterase Inhibition by Rivastigmine in Humans," J. Clin. Psychopharmacol., 1999, pp. 513-521, vol. 19, No. 6.
Kfoury, N. et al., "Trans-cellular Propagation of Tau Aggregation by Fibrillar Species," J. Bio. Chem., Jun. 1, 2012, pp. 19440-19451, vol. 287, No. 23.
Kim, J. et al., "The Stressed Hippocampus, Synaptic Plasticity and Lost Memories," Nat. Rev., Jun. 2002, pp. 453-462, vol. 3.
Klunk, W. et al., "Imaging Brain Amyloid in Alzheimer's Disease with Pittsburgh Compound-B," Ann. Neurol., 2004, pp. 306-319, vol. 55.
Kukull, W. et al., "Dementia and Alzheimer Disease Incidence," Arch. Neurol., Nov. 2002, pp. 1737-1746, vol. 59.
Kuo, Y-M. et al., "Water-soluble Abeta (N-40, N-42) Oligomers in Normal and Alzheimer Disease Brains," J. Biol. Chem., Feb. 23, 1996, pp. 4077-4081, vol. 271, No. 8.
Lam, F. et al., "Beta-Amyloid efflux mediated by p-glycoprotein," J. Neurochem., 2001, pp. 1121-1128, vol. 76.
Lame, M. et al., "Quantification of amyloid beta peptides AlphaBeta1-38, AlphaBeta1-40, and AlphaBeta1-42 in human cerebrospinal fluid by ultra-performance liquid chromatography-tandem mass spectrometry," Anal. Biochem., 2011, pp. 133-139, vol. 419, No. 2.
Lanz, T. et al., "Studies of Abeta Pharmacodynamics in the Brain, Cerebrospinal Fluid, and Plasma in Young (Plaque-Free) Tg2576 Mice Using the γ-Secretase Inhibitor N24(2S)-2-(3,5-Difluorophenyl)-2-hydroxyethanoyl]-N1-[(7S)-5-methyl-6-oxo-6,7-dihydro-5H-dibenzo[b,d]azepin-7-yl]-L-alaninamide (LY-411575)," J. Pharmacol. Exp. Ther., 2004, pp. 49-55, vol. 309, No. 1.
Lemaire et al., "Stabilization of Gas-Phase Noncovalent Macromolecular Complexes in Electrospray Mass Spectrometry Using Aqueous Triethylammonium Bicarbonate Buffer", Analytical Chemistry, 2001, pp. 1699-1706, vol. 73, No. 8.
Lewczuk, P. et al., "Amyloid β peptides in plasma in early diagnosis of Alzheimer's disease: A multicenter study with multiplexing," Experimental Neurology, Jun. 1, 2010, pp. 366-370, vol. 223, No. 2.
Mann, M. et al., "Analysis of Proteins and Proteomes by Mass Spectrometry," Annu. Rev. Biochem., 2001, pp. 137-473, vol. 70.
Martin, B. et al., "Intracellular Accumulation of beta-Amyloid in Cells Expressing the Swedish Mutant Amyloid Precursor Protein," J. Biol. Chem., Nov. 10, 1995, pp. 26727-26730, vol. 270, No. 45.
Mawuenyega, K. et al., "Decreased Clearance of CNS beta-Amyloid in Alzheimer's Disease," Science, Dec. 9, 2010, p. 1774, vol. 330, No. 6012, with Supporting Online Material, 9 pgs.
Mayeux, R. et al., "The Apolipoprotein E4 Allele in Patients with Alzheimer's Disease," Ann. Neurol., 1993, pp. 752-754, vol. 34.
Merchak, A. et al., "Use of Stable isotope labeling technique and mass isotopomer distribution analysis of [13C] palmitate isolated from surfactant disaturated phospholipids to study surfactant in vivo kinetics in a premature infant," J. Mass. Spectrom., 2000, pp. 734-738, vol. 35.
Morris, J. et al., "Mild Cognitive Impairment Represents Early-Stage Alzheimer Disease," Arch. Neural., 2001, pp. 397-405, vol. 58.
Morris, J. et al., "Pathologic Correlates of Nondemented Aging, Mild Cognitive Impairment, and Early-Stage Alzheimer's Disease," J. Mol. Neuro., 2001, pp. 101-118, vol. 17, Humana Press.
Murphy, M. et al., "Presenilin 1 Regulates Pharmacologically Distinct gamma-Secretase Activities," J. Biol. Chem., Aug. 25, 2000, pp. 26277-26284, vol. 275, No. 34.
NCBI dbSNP database Build 123, submitted SNP ss23860171 corresponding to rs1868402, Oct. 28, 2004; 4 pgs.
NCBI, Reference SNP(refSNP) Cluster Report: rs1060842, May 25, 2006; 4 pgs.
Nordin, C. et al., "Gradients of CSF Monoamine Metabolites: A Comparison Between Male and Female Volunteers," J. Psychiat. Res., 1995, pp. 133-140, vol. 29, No. 2.
Notice of Acceptance dated Jul. 27, 2011 from related Australian Patent Application No. 2006232338; 9 pgs.
Notice of Acceptance dated Aug. 12, 2014 from related Australian Patent Application No. 2009314110; 7 pgs.
Notice of Acceptance dated Dec. 10, 2014 from related Australian Patent Application No. 2011258462; 4 pgs.
Notice of Acceptance dated Sep. 21, 2015 from related Australian Patent Application No. 2012346476; 5 pgs.
Notice of Allowance dated Jun. 6, 2013 from related Canadian Patent Application No. 2,604,057; 1 pg.
Notice of Allowance dated Jan. 27, 2014 from related European Patent Application No. 06749116.7; 6 pgs.
Notice of Allowance dated Dec. 31, 2012 from related Chinese Patent Application No. 200680019537.6, 4 pgs., with English translation.
Notice of Allowance and Examiner-Initiated Interview Summary dated Oct. 12, 2010 from related U.S. Appl. No. 11/910,463; 9 pgs.
Notice of Allowance with Examiner-Initiated Interview Summary dated Mar. 26, 2012 from related U.S. Appl. No. 13/005,233; 8 pgs.
Notice of Decision from Post-Prosecution Pilot Program Conference dated Nov. 8, 2016 from related U.S. Appl. No. 13/699,497; 4 pgs.
Nguyen, K. et al., "Exposure to Acute Stress Induces Brain Interleukin-1beta Protein in the Rat," J. Neurosci., Mar. 15, 1998, pp. 2239-2246, vol. 18, No. 6.
Office Action dated Dec. 3, 2010 from related Australian Patent Application No. 2006232338; 2 pgs.
Office Action dated May 2, 2011 from related Australian Patent Application No. 2006232338; 2 pgs.
Office Action dated Dec. 11, 2013 from related Australian Patent Application No. 2009314110; 3 pgs.
Office Action dated Mar. 7, 2014 from related Australian Patent Application No. 2009314110; 3 pgs.
Office Action dated Jul. 16, 2014 from related Australian Patent Application No. 2011258462; 4 pgs.
Office Action dated Feb. 25, 2015 from related Australian Patent Application No. 2012346476; 3 pgs.
Office Action dated Dec. 16, 2016 from related Australian Patent Application No. 2012359020; 3 pgs.
Office Action dated Jan. 28, 2016 from related Australian Patent Application No. 2015201714; 5 pgs.
Office Action dated Dec. 16, 2016 from related Australian Patent Application No. 2013348049; 6 pgs.
Office Action dated Jul. 10, 2012 from related Canadian Patent Application No. 2,604,057; 3 pgs.
Office Action dated Sep. 8, 2016 from related Canadian Patent Application No. 2,890,758; 4 pgs.

(56) References Cited

OTHER PUBLICATIONS

Office Action dated Apr. 1, 2012 from related Chinese Patent Application No. 200680019537.6; 6 pgs.
Office Action dated Sep. 3, 2012 from related Chinese Patent Application No. 200680019537.6, 11 pgs., with English translation.
Office Action dated Jun. 8, 2010 from related Chinese Patent Application No. 200680019537.6, 15 pgs., with English translation.
Office Action dated Jul. 1, 2013 from related Chinese Patent Application No. 200980150353.7, 65 pgs., with English translation.
Office Action dated Mar. 12, 2014 with Search Report dated Mar. 4, 2014 from related Chinese Patent Application No. 200980150353.7; 49 pgs., with English translation.
Office Action dated Oct. 27, 2014 from related Chinese Patent Application No. 200980150353.7; 25 pgs., with English translation.
Office Action dated Oct. 14, 2013 from related European Patent Application No. 06749116.7; 8 pgs.
Office Action dated Feb. 3, 2012 from related European Patent Application No. 06749116.7; 9 pgs.
Office Action dated Aug. 29, 2014 from related European Patent Application No. 09826718.0; 5 pgs.
Office Action dated Oct. 1, 2013 from related European Patent Application No. 09826718.0; 5 pgs.
Office Action dated Feb. 6, 2015 from related European Patent Application No. 11787251.5; 5 pgs.
Office Action dated Aug. 16, 2016 from related European Patent Application No. 12853146.4; 4 pgs.
Office Action dated May 2, 2014 from related Indian Patent Application No. 5008/CHENP/2007; 6 pgs.
Office Action dated Jul. 19, 2012 from related Indian Patent Application No. 5008/CHENP/2007; 2 pgs.
Office Action dated May 22, 2012 from related Japanese Patent Application No. 2008-505406; 9 pgs., with English translation.
Office Action dated May 24, 2011 from related Japanese Patent Application No. 2008-505406; 6 pgs., with English translation.
Office Action dated Oct. 18, 2011 from related Japanese Patent Application No. 2008-505406; 4 pgs., with English translation.
Office Action dated Oct. 28, 2014 from related Japanese Patent Application No. 2011-536454; 5 pgs., English translation only.
Office Action dated Dec. 10, 2013 from related Japanese Patent Application No. 2011-536454; 4 pgs., with English translation.
Office Action dated Aug. 19, 2014 from related Japanese Patent Application No. 2013-512165; 6 pgs., with English translation.
Office Action dated Jun. 23, 2015 from related Japanese Patent Application No. 2013-512165; 3 pgs., with English translation.
Office Action dated Jul. 8, 2015 from related Japanese Patent Application No. 2014-537173; 7 pgs., with English translation.
Office Action dated Mar. 9, 2016 from related Japanese Patent Application No. 2014-537173; 3 pgs., with partial English translation.
Office Action dated Jul. 12, 2016 from related Japanese Patent Application No. 2014-548837; 9 pgs., with English translation.
Office Action dated Nov. 22, 2016 from related Japanese Patent Application No. 2016-023884; 6 pgs., with English translation.
Office Action dated Dec. 30, 2008 from related U.S. Appl. No. 11/910,463; 6 pgs.
Office Action dated Feb. 23, 2010 from related U.S. Appl. No. 11/910,463; 19 pgs.
Office Action dated Sep. 4, 2009 from related U.S. Appl. No. 12/108,065; 18 pgs.
Ando, S. et al., "Turnover of Myelin Lipids in Aging Brain," Neurochem. Res., Jan. 2003, pp. 5-13, vol. 28, No. 1.
Applicant Initiated Interview Summary dated Feb. 19, 2016 with Applicant Summary of Interview filed May 3, 2016 from related U.S. Appl. No. 13/699,497; 2 pgs.
Applicant Initiated Interview Summary dated Dec. 14, 2016 held on Dec. 8, 2016 from related U.S. Appl. No. 13/699,497; 2 pgs.
Bahmanyar, S. et al., "Localization of Amyloid beta Protein Messenger RNA in Brains from Patients with Alzheimer's Disease," Science, Jul. 3, 1987, pp. 77-80, vol. 237.
Bale, T. et al., "CRF and CRF Receptors: Role in Stress Responsivity and Other Behaviors," Annu. Rev. Pharmacol. Toxicol., 2004, pp. 525-557, vol. 44.
Bateman, R. et al., "A Gamma-Secretase Inhibitor Decreases Amyloid-beta Production in the Central Nervous System," NIH Public Access Author Manuscript, Jul 1. 2010, pp. 1-12; Ann. Neurol., Jul. 2009, pp. 48-54, vol. 66, No. 1.
Bateman, R. et al., "Stable Isotope Labeling Tandem Mass Spectrometry (SILT) to Quantify Protein Production and Clearance Rates," J. Am. Soc. Mass. Spectrom., 2007, pp. 997-1006, vol. 18.
Bateman, R. et al., "Fluctuations of CSF amyloid-beta levels: Implications for a diagnostic and therapeutic biomarker," Neurology, Feb. 27, 2007, pp. 666-669, vol. 68.
Bateman, R. et al., "Quantifying CNS protein production and clearance rates in humans using in vivo stable isotope labeling, immunoprecipitation, and tandem mass spectrometry," NIH Public Access Author Manuscript, Nov. 17, 2010, pp. 1-14; Nat. Med., Jul. 2006, pp. 856-861, vol. 12, No. 7.
Bateman, R. et al., "Human amyloid-beta synthesis and clearance rates as measured in cerebrospinal fluid in vivo," Nat. Med., Jul. 2006, pp. 856-861, vol. 12, No. 7.
Bateman R. et al., "Clinical and Biomarker Changes in Dominantly Inherited Alzheimer's Disease," NIH Public Access Author Manuscript, Feb. 28, 2013, pp. 1-16; N. Eng. J. Med., Aug. 30, 2012, pp. 795-804, vol. 367, No. 9.
Berg, L. et al., "Clinicopathologic Studies in Cognitively Healthy Aging and Alzheimer Disease," Arch. Neurol., 1998, pp. 326-335, vol. 55.
Bibl, M. et al., "CSF amyloid-beta-peptides in Alzheimer's disease, dementia with Lewy bodies and Parkinson's disease dementia," Brain, May 2006, pp. 1177-1187, vol. 129, Part 5.
BOLUS (medicine), definition from Wikipedia, retrieved from internet on Jan. 28, 2016, 2 pgs.
Bonifacino, J. et al., "Immunoprecipitation Using Cells in Suspension Lysed With a Nondenaturing Detergent Solution," Curr. Prot. Protein Sci., 1999, pp. 9.8.1 to 9.8.28, Unit 9.8, Supplement 18.
Cirrito, J. et al, "In Vivo Assessment of Brain Interstitial Fluid with Microdialysis Reveals Plaque-Associated Changes in Amyloid-beta Metabolism and Half-Life," J. Neurosci., Oct. 1, 2003, pp. 8844-8853, vol. 23, No. 26.
Cirrito, J. et al., "P-glycoprotein deficiency at the blood-brain barrier increases amyloid-beta deposition in an Alzheimer disease mouse model," J. Clin. Invest., Nov. 2005, pp. 3285-3290, vol. 115, No. 11.
Communication Under Rule 71(3) EPC, Intention to Grant, dated Nov. 2, 2015, from related European Patent Application No. 11787251.5, 35 pgs.
Communication Under Rule 71(3) EPC, Intention to Grant, dated Jan. 27, 2014, from related European Patent Application No. 06749116.7, 56 pgs.
Cook, J. et al, "Acute Gamma-Secretase Inhibition of Nonhuman Primate CNS Shifts Amyloid Precursor Protein (APP) Metabolism from Amyloid-β Production to Alternative APP Fragments without Amyloid-β Rebound," J. Neurosci., May 12, 2010, pp. 6743-6750, vol. 30, No. 19.
Corder, E. et al, "Gene Dose of Apolipoprotein E Type 4 Allele and the Risk of Alzheimer's Disease in Late Onset Families," Science, Aug. 13, 1993, pp. 921-923, vol. 261.
Corder, E. et al., "No Increased Risk of the Apolipoprotein E ε2 Allele with Early-Onset Alzheimer's Disease," Annals of Neurology, Mar. 1996, pp. 414-416, vol. 39, No. 3.
Corder, E. et al., "The Apolipoprotein E E4 Allele and Sex-Specific Risk of Alzheimer's Disease," JAMA, Feb. 1, 1995, pp. 373-374, vol. 273, No. 5.
Cruchaga, C. et al., "SNPs Associated with Cerebrospinal Fluid Phospho-Tau Levels Influence Rate of Decline in Alzheimer's Disease," PLoS Genetics, Sep. 2010, pp. 1-10, vol. 6, Issue 9, e1001101.
Cutler, N. et al., "Dose-dependent CSF acetylcholinesterase inhibition by SDZ ENA 713 in Alzheimer's disease," Acta. Neurol. Scand., 1998, pp. 244-250, vol. 97.

(56) References Cited

OTHER PUBLICATIONS

Demattos, R. et al., "ApoE and Clusterin Cooperatively Suppress Abeta Levels and Deposition: Evidence that ApoE Regulates Extracellular Abeta Metabolism in Vivo," Neuron, Jan. 22, 2004, pp. 193-202, vol. 41.
Demattos, R. et al., "Peripheral anti-Abeta antibody alters CNS and plasma Abeta clearance and decreases brain Abeta burden in a mouse model of Alzheimer's disease," PNAS, Jul. 17, 2001, pp. 8850-8855, vol. 98, No. 15.
Elbert, D. et al., "Stable Isotope Labeling Tandem Mass Spectrometry (SILT): Integration with Peptide Identification and Extension to Data-Dependent Scans," J. Proteome Res., Oct. 2008, pp. 4546-4556, vol. 7, No. 10.
Elias, N. et al., "In Vivo Metabolism of ApoB, ApoA-I, and VLDL Triglycerides in a Form of Hypobetalipoproteinemia Not Linked to the ApoB Gene," Arterioscler. Thromb. Vasc. Biol., 2000, pp. 1309-1315, vol. 20.
Extended European Search Report dated Apr. 8, 2009 from related European Patent Application No. 06749116.7; 11 pgs.
Extended European Search Report dated Sep. 3, 2012 from related European Patent Application No. 09826718.0; 10 pgs.
Extended European Search Report dated Nov. 4, 2013 from related European Patent Application No. 11787251.5; 5 pgs.
Extended European Search Report dated Feb. 23, 2015 from related European Patent Application No. 12853146.4; 5 pgs.
Extended European Search Report dated Jan. 20, 2016 from related European Patent Application No. 12859548.5; 11 pgs.
Extended European Search Report dated Mar. 31, 2016 from related European Patent Application No. 13856598.1; 7 pgs.
Extended European Search Report dated Jul. 20, 2016 from related European Patent Application No. 16158001.4; 5 pgs.
Fagan, A. et al., "Human and Murine ApoE Markedly Alters Abeta Metabolism before and after Plaque Formation in a Mouse Model of Alzheimer's Disease," Neurobiol. Disease, 2002, pp. 305-318, vol. 9.
Fagan, A. et al., "Cerebrospinal fluid tau/beta-amyloid 42 ratio as a prediction of cognitive decline in nondemented older adults," Arch. Neurology, Mar. 2007, pp. 343-349, vol. 64.
Fryer, J. et al., "Human Apolipoprotein E4 Alters the Amyloid-beta 40:42 Ratio and Promotes the Formation of Cerebral Amyloid Angiopathy in an Amyloid Precursor Protein Transgenic Model," J. Neurosci., Mar. 16, 2005, pp. 2803-2810, vol. 25, No. 11.
Fukumoto, H. et al., "APOE [epsilon]3/[epsilon]4 heterozygotes have an elevated proportion of apolipoprotein E4 in cerebrospinal fluid relative to plasma, independent of Alzheimer's disease diagnosis," Exp. Neurology, Sep. 1, 2003, pp. 249-253, vol. 183, No. 1.
Fukuyama, R. et al., "Age-Dependent Change in the Levels of AlphaBetarβ40 and AlphaBeta42 in Cerebrospinal Fluid from Control Subjects, and a Decrease in the Ratio of AlphaBeta42 to AlphaBeta40 Level in Cerebrospinal Fluid from Alzheimer's Disease Patients," Eur. Neurol. , Jan. 1, 2000, pp. 155-160, vol. 43, No. 3.
Games, D. et al., "Alzheimer-type neuropathology in transgenic mice overexpressing V717F beta-amyloid precursor protein," Nature, Feb. 9, 1995, pp. 523-527, vol. 373.
Gersovitz, M. et al., "Albumin Synthesis in Young and Elderly Subjects Using a New Stable Isotope Methodology: Response to Level of Protein Intake," Metabolism, Nov. 1980, pp. 1075-1086, vol. 29, No. 11.
Giedraitis, V. et al., "The normal equilibrium between CSF and plasma amyloid beta levels is disrupted in Alzheimer's disease," Neuroscience Letters, Oct. 29, 2007, pp. 127-131, vol. 427, No. 3.
Gregg, R. et al., "Apolipoprotein E metabolism in normolipoproteinemic human subjects," J. Lipid Res., Jan. 1, 1984, pp. 1167-1176, vol. 25.
Grundy, S. et al., "Kinetic Mechanisms Determining Variability in Low Density Lipoprotein Levels and Rise with Age," Arteriosclerosis, Nov./Dec. 1985, pp. 623-630, vol. 5.
Haas, D. et al., "Evidence of a Source of HIV Type 1 within the Central Nervous System by Ultraintensive Sampling of Cerebrospinal Fluid and Plasma," Aids Research & Human Retroviruses, Nov. 15, 2000, pp. 1491-1502, vol. 16, No. 15.
Haas, et al., "Two phases of HIV RNA decay in CSF during initial days of multidrug therapy," Neurology, 2003, pp. 1391-1396, vol. 61.
Hansson, O. et al., "Prediction of Alzheimer's Disease Using the CSF AlphaBeta42/AlphaBeta40 Ratio in Patients with Mild Cognitive Impairment," Dement. Geriatr. Cogn. Disord., Jan. 1, 2007, pp. 316-320, vol. 23, No. 5.
Office Action dated Mar. 31, 2010 from related U.S. Appl. No. 12/267,974; 12 pgs.
Office Action dated Sep. 24, 2010 from related U.S. Appl. No. 12/267,974; 11 pgs.
Office Action dated May 8, 2014 from related U.S. Appl. No. 12/267,974; 15 pgs.
Office Action dated Jun. 4, 2013 from related U.S. Appl. No. 13/055,569; 18 pgs.
Office Action dated Mar. 7, 2014 from related U.S. Appl. No. 13/055,569; 18 pgs.
Office Action dated Jan. 15, 2015 from related U.S. Appl. No. 13/055,569; 13 pgs.
Office Action dated Jun. 27, 2011 from related U.S. Appl. No. 13/005,233; 12 pgs.
Office Action dated Apr. 4, 2012 from related U.S. Appl. No. 13/129,036; 12 pgs.
Office Action dated Mar. 22, 2013 from related U.S. Appl. No. 13/129,036; 13 pgs.
Office Action dated Oct. 16, 2014 from related U.S. Appl. No. 13/129,036; 16 pgs.
Office Action dated Nov. 2, 2012 from related U.S. Appl. No. 13/534,704; 4 pgs.
Office Action dated Oct. 25, 2013 from related U.S. Appl. No. 13/534,704; 6 pgs.
Office Action dated Dec. 30, 2013 from related U.S. Appl. No. 13/699,497; 15 pgs.
Office Action dated Aug. 12, 2014 from related U.S. Appl. No. 13/699,497; 13 pgs.
Office Action dated Feb. 8, 2016 from related U.S. Appl. No. 13/699,497; 15 pgs.
Office Action dated Aug. 4, 2016 from related U.S. Appl. No. 13/699,497; 10 pgs.
Office Action dated May 22, 2015 from related U.S. Appl. No. 14/224,933; 8 pgs.
Office Action dated Sep. 25, 2015 from related U.S. Appl. No. 14/352,560; 8 pgs.
Office Action dated Jan. 16, 2015 from related U.S. Appl. No. 14/366,831; 18 pgs.
Office Action dated Aug. 24, 2015 from related U.S. Appl. No. 14/366,831; 23 pgs.
Office Action dated Sep. 1, 2015 from related U.S. Appl. No. 14/523,148; 14 pgs.
Office Action dated Sep. 30, 2016 from related U.S. Appl. No. 14/944,311; 9 pgs.
Olsson, A. et al., "Measurement of alpha- and beta-secretase cleaved amyloid precursor protein in cerebrospinal fluid from Alzheimer patients," Exp. Neurol., 2003, pp. 74-80, vol. 183.
Oosterkamp et al., "Quantitative Peptide Bioanalysis Using Column-switching Nano Liquid Chromatography/Mass Spectrometry", J. Mass Spectrometry, 1998, pp. 976-983, vol. 33.
Patterson, B. et al., "Incorporation of a stable isotopically labeled amino acid into multiple human apolipoproteins," J. Lipid Res., Jul. 1, 1991, pp. 1063-1072, vol. 32, No. 7.
Patterson, B. et al., "Use of stable isotopically labeled tracers to measure very low density lipoprotein-triglyceride turnover," J. Lipid Res., 2002, pp. 223-233, vol. 43.
Patterson, B., "Use of Stable Isotopically Labeled Tracers for Studies of Metabolic Kinetics: An Overview," Metabolism, Mar. 1997, pp. 322-329, vol. 46, No. 3.
Patterson, B. et al., "Age and Amyloid Effects on Human CNS Amyloid-Beta Kinetics," Ann. Neurol., undated draft Research Article, In press., John Wiley & Sons, pp. 1-28 with cover page.

(56) References Cited

OTHER PUBLICATIONS

Pinto, et al., "Plasma Kinetics of a Cholesterol-Rich Emulsion in Young, Middle-Aged, and Elderly Subjects," Lipids, 2001, pp. 1307-1311, vol. 36, No. 12.

Pitas, et al., "Astrocytes synthesize apolipoprotein E and metabolize apolipoprotein E-Containing lipoproteins," Biochim. Biophys. Acta., 1987, pp. 148-161, vol. 917.

Potter, R. et al., "Increased in vivo amyloid-beta42 production, exchange, and irreversible loss in presenilin mutations carriers," NIH Public Access Author Manuscript, Nov. 24, 2013, pp. 1-19; Sci. Transl. Med., Jun. 12, 2013, pp. 1-10, vol. 5, Issue 189, Article No. 189ra77.

Price, J. et al., "Neuron Number in the Entorhinal Cortex and CA1 in Preclinical Alzheimer Disease," Arch. Neurol., Sep. 2001, pp. 1395-1402, vol. 58.

Qiu, W. et al., "Degradation of Amyloid beta-Protein by a Serine Protease-alpha-2-Macroglobulin Complex," J. Biol. Chem., Apr. 5, 1996, pp. 8443-8451, vol. 271, No. 14.

Results of Telephone Consultation dated Jul. 24, 2013 from related European Patent Application No. 06749116.7; 6 pgs.

Results of Telephone Consultation dated Oct. 14, 2013 from related European Patent Application No. 06749116.7; 3 pgs.

Rhoads, T. et al., "Measuring Copper and Zinc Superoxide Dismutase from Spinal Cord Tissue Using Electrospray Mass Spectrometry," NIH Public Access Author Manuscript, Aug. 2012, pp. 1-15; Anal. Biochem., Aug. 1, 2011, pp. 52-58, vol. 415, No. 1.

Rosman, K.J.R. et al., "Isotopic Compositions of the Elements 1997," Pure & Appl. Chem., 1998, pp. 217-235, vol. 70, No. 1.

Sanchez, L. et al., "ABeta40 and ABeta42 Amyloid Fibrils Exhibit Distinct Molecular Recycling Properties," J. Am. Chem. Soc., Apr. 12, 2011, pp. 6505-6508, vol. 133, No. 17.

Savage, M. et al., "Turnover of Amyloid beta-Protein in Mouse Brain and Acute Reduction of Its Level by Phorbol Ester," J. Neurosci., Mar. 1, 1998, pp. 1743-1752, vol. 18, No. 5.

Schulte, J. et al., "Effects of Resistance Training on the Rate of Muscle Protein Synthesis in Frail Elderly People," Int. J. Sport Nutr. Exerc. Metab., 2001, pp. S111-S118, vol. 11.

Shibata, et al., "Clearance of Alzheimer's amyloid-beta 1-40 peptide from brain by LDL receptor-related protein-1 at the blood-brain barrier," J. Clin. Invest., 2000, pp. 1489-1499, vol. 106, No. 12.

Shoji, M., "Cerebrospinal Fluid ABeta40 and ABeta42: Natural Course and Clinical Usefulness," Front. Biosci., Apr. 1, 2002, pp. d997-1006, vol. 7.

Smith, Q. et al., "Kinetics of Neutral Amino Acid Transport Across the Blood-Brain Barrier," J. Neurochem., 1987, pp. 1651-1658, vol. 49, No. 5.

Supplementary European Search Report dated Apr. 8, 2009 from related European Patent Application No. 06749116.7, 11 pgs.

Talbot, C. et al., "Protection against Alzheimer's disease with apoE E2," Lancet, Jun. 4, 1994, pp. 1432-1433, vol. 343.

Tamaoka, A. et al., "Amyloid-beta-protein isoforms in brain of subjects with PS1-linked, betaAPP-linked and sporadic Alzheimer disease," Molecular Brain Res., May 1, 1998, pp. 178-185, vol. 56, No. 1-2.

Tan, Y. et al., "Central alpha-adrenergic receptors and corticotropin releasing factor mediate hemodynamic responses to acute cold stress," Brain Res., 2003, pp. 122-129, vol. 968.

Vickers, J., "A Vaccine Against Alzheimer's Disease, Developments to Date," Drugs Aging, 2002, pp. 487-494, vol. 19, No. 7.

Vogelgesang, S. et al., "The Role of P-glycoprotein in Cerebral Amyloid Angiopathy; Implications for the Early Pathogenesis of Alzheimer's Disease," Cur. Alzheimer Res., 2004, pp. 121-125, vol. 1.

Vogelgesang, S. et al., "Deposition of Alzheimer's beta-amyloid is inversely correlated with P-glycoprotein expression in the brains of elderly non-demented humans," Pharmacogenetics, 2002, pp. 535-541, vol. 12.

Wahrle, S. et al., "Differential metabolism of ApoE isoforms in plasma and CSF," Exp. Neurology, Sep. 1, 2003, pp. 1-6, vol. 183, No. 1.

Wang, R. et al., "The Profile of Solube Amyloid beta Protein in Cultured Cell Media," J. Biol. Chem., Dec. 13, 1996, pp. 31894-31902, vol. 271, No. 50.

Williams, M., "Spinal catheter insertion via seated lumbar puncture using a massage chair," Neurology, Jun. 2002, pp. 1859-1860, vol. 58.

Wisniewski, K. et al., "Occurrence of Neuropathological Changes and Dementia of Alzheimer's Disease in Down's Syndrome," Ann. Neurol., 1985, pp. 278-282, vol. 17.

Yarasheski, K. et al., "Reducing plasma HIV RNA improves muscle amino acid metabolism," Am. J. Physiol. Endocrinol. Metab., Jan. 2005, pp. E278-E284, vol. 288, No. 1.

Yarasheski, K. et al., "Increased plasma Gln and Leu Ra and inappropriately low muscle protein synthesis rate in AIDS wasting," Am. Physiol. Soc., 1998, pp. E577-E583.

Yarasheski, K. et al., "Measurement of Muscle Protein Fractional Synthetic Rate by Capillary Gas Chromatography/Combustion Isotope Ratio Mass Spectrometry," Biol. Mass. Spectrom., 1992, pp. 486-490, vol. 21, John Wiley & Sons.

Yarasheski, K., "Exercise, Aging, and Muscle Protein Metabolism," J. Gerontol., 2003, pp. 918-922, vol. 58A, No. 10.

Yarasheski, "Managing Sarcopenia with Progressive Resistance Exercise Training," J. Nutrition Health & Aging, 2002, pp. 1-8, vol. 6, No. 5.

Potter, R. et al., "Amyloid-beta 42:40 Metabolism Is Altered in Autosomal Dominant Alzheimer's Disease (ADAD)," Annals of Neurology, 136th Annual Meeting, Sep. 27, 2011 Works in Progress Poster Session, pp. S88-S89, T1541, vol. 70, Supplement 15.

Office Action dated Mar. 9, 2017 from related U.S. Appl. No. 15/422,165; 9 pgs.

Office Action dated Mar. 10, 2017 from related U.S. Appl. No. 13/699,497; 16 pgs.

Office Action dated Apr. 12, 2017 from related Canadian Patent Application No. 2,800,680; 4 pgs.

Communication Under Rule 71(3) EPC, Intention to Grant, dated Apr. 19, 2017, from related European Patent Application No. 12859548.5; 133 pgs.

Office Action dated Apr. 21, 2017 from related U.S. Appl. No. 15/080,230; 14 pgs.

Communication Under Rule 71(3) EPC, Intention to Grant, dated Apr. 24, 2017, from related European Patent Application No. 16158001.4; 70 pgs.

Office Action dated May 25, 2017 from related Australian Patent Application No. 2017200029; 2 pgs.

Eisenberg, D. et al., "The Amyloid State of Proteins in Human Disease," Cell, Mar. 16, 2012, pp. 1188-1203, vol. 148, No. 6, Elsevier Inc.

Zhang, W. et al., "A Highly Selective and Specific PET Tracer for Imaging of Tau Pathologies," J. Alzheimer's Disease, 2012, pp. 601-612, vol. 31, No. 3.

Office Action dated Jul. 13, 2017 from related U.S. Appl. No. 15/057,694; 15 pgs.

Crisp, M. et al., "In vivo kinetic approach reveals slow SOD1 turnover in the CNS," J. Clin. Invest., Jul. 2015, pp. 2772-2780, vol. 125, No. 7.

Office Action dated Aug. 8, 2017 from related Japanese Patent Application No. 2016-023884; 5 pgs., with English translation.

Notice of Allowance dated Jan. 25, 2018 from Canadian Patent Application No. 2,800,680; 1 pg.

Office Action dated Nov. 2, 2017 from related U.S. Appl. No. 15/080,230; 21 pgs.

Examiner's Answer dated Jan. 26, 2018 from related U.S. Appl. No. 13/699,497; 14 pgs.

Office Action dated Nov. 30, 2018 from related Indian Patent Application No. 4816/CHEN/2014; 5 pgs.

Office Action dated Feb. 1, 2019 from related European Patent Application No. 15846448.7; 4 pgs.

Barthelemy, N. et al., "Tau hyperphosphorylation on T217 in cerebrospinal fluid is specifically associated to amyloid-beta pathology," bioRxiv, Nov. 30, 2017, pp. 1-20, and Supplementary Information, pp. 1-21.

(56) References Cited

OTHER PUBLICATIONS

International Search Report and Written Opinion dated Aug. 28, 2019 from related International Patent Application No. PCT/US2019/030725; 44 pgs.
Notice of Allowance dated Feb. 4, 2020 from related European Patent Application No. 15846448.7; 51 pgs.
Office Action dated Jun. 13, 2019 from related European Patent Application No. 15846448.7; 3 pgs.
Office Action dated Jun. 25, 2019 from related Japanese Patent Application No. 2017-517320; 5 pgs.

* cited by examiner

1    MAEPRQEFEV MEDHAGTYGL GDRKDQGGYT MHQDQEGDTD AGLKESPLQT PTEDGSEEPG SETSDAKSIP TAEDVTAPLV

81   DEGAPGKQAA AQPHTEIPEG TTAEEAGIGD TPSLEDEAAG HVTQARMVSK SKDGTGSDDK KAKGADGKTK IATPRGAAPP

161  GQKGQANATR IPAKTPPAPK TPPSSGEPPK SGDTSTPGSP GSPGTPGSRS RTPSLPTPPT REPKKVAVVR TPPKSPSSAK

241  SRLQTAPVPM PDLKNVKSKI GSTENLKHQP GGGKVQIINK KLDLSNVQSK CGSKDNIKHV PGGGSVQIVY KPVDLSKVTS

321  KCGSLGNIHH KPGGGQVEVK SEKLDFKDRV QSKIGSLDNI THVPGGGNKK IETHKLTFRE NAKAKTDHGA EIVYKSPVVS

401  GDTSPRHLSN VSSTGSIDMV DSPQLATLAD EVSASLAKQG L

FIG. 2A

SEQUENCE LISTING

<160> NUMBER OF SEQ ID NOS: 7

<210> SEQ ID NO 1
<211> LENGTH: 441
<212> TYPE: PRT
<213> ORGANISM: Homo sapiens -continued

```
<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met Gly
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
```

```
            405                 410                 415
Ile Asp Met Val Asp Ser Pro Gln Leu Ala Thr Leu Ala Asp Glu Val
        420                 425                 430

Ser Ala Ser Leu Ala Lys Gln Gly Leu
        435                 440

<210> SEQ ID NO 2
<211> LENGTH: 10
<212> TYPE: PRT
<213> ORGANISM: Homo sapiens

<400> SEQUENCE: 2

Thr Pro Ser Leu Pro Thr Pro Pro Thr Arg
1               5                   10

<210> SEQ ID NO 3
<211> LENGTH: 5
<212> TYPE: PRT
<213> ORGANISM: Homo sapiens

<400> SEQUENCE: 3

Arg Ser Gly Tyr Ser
1               5

<210> SEQ ID NO 4
<211> LENGTH: 8
<212> TYPE: PRT
<213> ORGANISM: Homo sapiens

<400> SEQUENCE: 4

Ile Gly Ser Thr Glu Asn Leu Lys
1               5

<210> SEQ ID NO 5
<211> LENGTH: 19
<212> TYPE: PRT
<213> ORGANISM: Homo sapiens

<400> SEQUENCE: 5

His Val Pro Gly Gly Gly Ser Val Gln Ile Val Tyr Lys Pro Val Asp
1               5                   10                  15

Leu Ser Lys

<210> SEQ ID NO 6
<211> LENGTH: 20
<212> TYPE: PRT
<213> ORGANISM: Homo sapiens

<400> SEQUENCE: 6

Ser Thr Pro Thr Ala Glu Asp Val Thr Ala Pro Leu Val Asp Glu Gly
1               5                   10                  15

Ala Pro Gly Lys
            20

<210> SEQ ID NO 7
<211> LENGTH: 12
<212> TYPE: PRT
<213> ORGANISM: Homo sapiens

<400> SEQUENCE: 7

Leu Gln Thr Ala Pro Val Pro Met Pro Asp Leu Lys
1               5                   10
```

TAU KINETIC MEASUREMENTS

CROSS REFERENCE TO RELATED APPLICATIONS

This application claims priority to PCT application number PCT/US2015/053283, filed Sep. 30, 2015, which claims the benefit of U.S. provisional application No. 62/057,853, filed Sep. 30, 2014, each of which is hereby incorporated by reference in its entirety.

GOVERNMENTAL RIGHTS

This invention was made with government support under R-01-NS065667 awarded by the National Institutes of Health. The government has certain rights in the invention.

FIELD OF THE INVENTION

The invention relates to in vitro methods for measuring the in vivo metabolism of tau in a subject.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND OF THE INVENTION

Neurofibrillary tangles (NFTs) in Alzheimer disease and other tauopathies are composed of insoluble hyperphosphorylated tau protein, but the mechanisms underlying the conversion of highly soluble tau into insoluble NFTs remain elusive. A need exists, therefore, for sensitive, accurate, and reproducible methods for measuring the in vivo metabolism of tau in the CNS.

SUMMARY OF THE INVENTION

One aspect of the invention provides methods for measuring the in vivo metabolism of tau by detecting the amount of labeled tau and unlabeled tau in one or more biological samples obtained from a subject who has received a labeled moiety, and determining the ratio of labeled tau to unlabeled tau in the biological sample.

Another aspect of the invention provides a method for measuring the metabolism of tau in a subject, the method comprising: (a) administering at least one labeled amino acid to the subject on one or more days; (b) collecting at least one biological sample from the subject between about day 1 and about day 20, about day 20 and about day 40, about day 40 and about day 100, or a combination thereof; (c) detecting and measuring the amount of labeled tau and/or the amount of unlabeled tau in each biological sample; and (d) calculating the metabolism of tau using the measurements from step (c), wherein the amount of labeled tau in the biological sample at a given time reflects the metabolism of tau.

Another aspect of the invention provides a method for measuring the metabolism of tau in a subject, the method comprising: (a) administering at least one labeled amino acid to the subject on one or more days; (b) collecting at least one biological sample from the subject between about day 2 and about day 20, about day 20 and about day 40, about day 40 and about day 100, or a combination thereof; (c) detecting and measuring the amount of labeled tau and/or the amount of unlabeled tau in each biological sample; and (d) calculating the metabolism of tau using the measurements from step (c), wherein the amount of labeled tau in the biological sample at a given time reflects the metabolism of tau.

Another aspect of the invention provides a method for measuring the metabolism of tau in a subject, the method comprising: (a) administering at least one labeled amino acid to the subject on two or more days; (b) collecting at least one biological sample from the subject between about day 1 and about day 20, about day 20 and about day 40, about day 40 and about day 100, or a combination thereof; (c) detecting and measuring the amount of labeled tau and/or the amount of unlabeled tau in each biological sample; and (d) calculating the metabolism of tau using the measurements from step (c), wherein the amount of labeled tau in the biological sample at a given time reflects the metabolism of tau.

Another aspect of the invention provides a method for measuring the metabolism of tau in a subject, the method comprising: (a) administering at least one labeled amino acid to the subject on two or more days; (b) collecting at least one biological sample from the subject between about day 2 and about day 20, about day 20 and about day 40, about day 40 and about day 100, or a combination thereof; (c) detecting and measuring the amount of labeled tau and/or the amount of unlabeled tau in each biological sample; and (d) calculating the metabolism of tau using the measurements from step (c), wherein the amount of labeled tau in the biological sample at a given time reflects the metabolism of tau.

Another aspect of the invention provides an in vitro method for measuring the metabolism of tau in a subject, the method comprising: (a) detecting and measuring the amount of labeled tau and/or the amount of unlabeled tau in each biological sample obtained from the subject; and (b) calculating the metabolism of tau using the amount of labeled and/or unlabeled tau determine in step (a), wherein the amount of labeled tau in the biological sample at a given time reflects the metabolism of tau; and wherein (i) the label was administered to the subject on one or more days, and (ii) each biological sample was collected from the subject between day 1 and day 20, day 20 and day 40, day 40 and day 100, or a combination thereof.

Another aspect of the invention provides an in vitro method for measuring the metabolism of tau in a subject, the method comprising: (a) detecting and measuring the amount of labeled tau and/or the amount of unlabeled tau in each biological sample obtained from the subject; and (b) calculating the metabolism of tau using the amount of labeled and/or unlabeled tau determine in step (a), wherein the amount of labeled tau in the biological sample at a given time reflects the metabolism of tau; and wherein (i) the label was administered to the subject on one or more days, and (ii) each biological sample was collected from the subject between day 2 and day 20, day 20 and day 40, day 40 and day 100, or a combination thereof.

Another aspect of the invention provides an in vitro method for measuring the metabolism of tau in a subject, the method comprising: (a) detecting and measuring the amount of labeled tau and/or the amount of unlabeled tau in each biological sample obtained from the subject; and (b) calculating the metabolism of tau using the amount of labeled and/or unlabeled tau determine in step (a), wherein the amount of labeled tau in the biological sample at a given time reflects the metabolism of tau; and wherein (i) the label was administered to the subject on two or more days, and (ii) each biological sample was collected from the subject between day 1 and day 20, day 20 and day 40, day 40 and day 100, or a combination thereof.

Another aspect of the invention provides an in vitro method for measuring the metabolism of tau in a subject, the method comprising: (a) detecting and measuring the amount of labeled tau and/or the amount of unlabeled tau in each biological sample obtained from the subject; and (b) calculating the metabolism of tau using the amount of labeled and/or unlabeled tau determine in step (a), wherein the amount of labeled tau in the biological sample at a given time reflects the metabolism of tau; and wherein (i) the label was administered to the subject on two or more days, and (ii) each biological sample was collected from the subject between day 1 and day 20, day 20 and day 40, day 40 and day 100, or a combination thereof.

An additional aspect of the invention encompasses kits for measuring the in vivo metabolism of neurally derived proteins in a subject, whereby the metabolism of the protein may be used as a predictor of a neurological or neurodegenerative disease, a monitor of the progression of the disease, or an indicator of the effectiveness of a treatment for the disease.

BRIEF DESCRIPTION OF THE FIGURES

The application file contains at least one photograph executed in color. Copies of this patent application publication with color photographs will be provided by the Office upon request and payment of the necessary fee.

FIG. 2A-C depicts tau digestion by trypsin. (A) Amino acid sequence of human full length tau (2N4R; SEQ ID NO: 1). Leucines are labeled in red. Amino acid sequences underlined and in blue identify leucine-containing fragments of tau that are produced by enzymatic cleavage with trypsin. The tryptic peptide fragment used for quantitation is TPSLPTPPTR (SEQ ID NO:2). The epitope recognized by the anti-tau antibody used in these experiments is RSGYS (SEQ ID NO: 3). (B) Chromatograms of the tau tryptic peptides identified in (A). The peptides were eluted according to their hydrophobicity. From top to bottom: IGSTENLK (SEQ ID NO: 4), TPSLPTPPTR (SEQ ID NO: 2), (HVPGGGSVQIVYKPVDLSK (SEQ ID NO: 5), STPTAEDVTAPLVDEGAPGK (SEQ ID NO: 6), and LQTAPVPMPDLK (SEQ ID NO: 7). (C) Standard curve of TPSLPTPPTR (SEQ ID NO: 2).

DETAILED DESCRIPTION

Figure 1A:
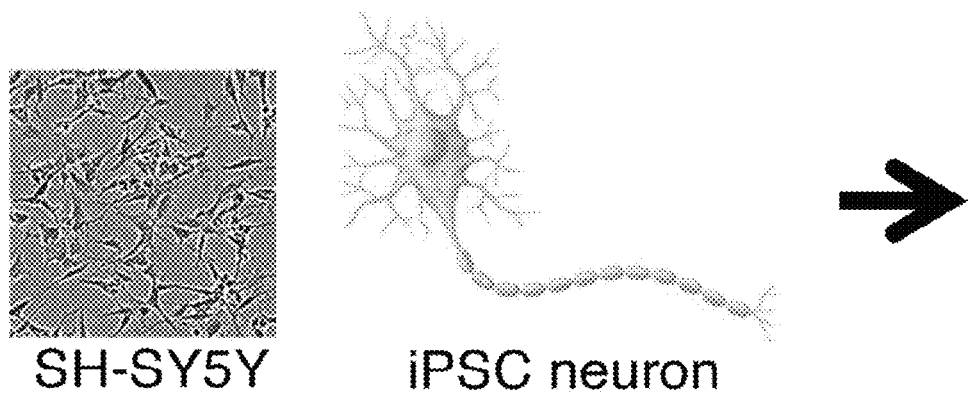
FIG. 1A-C depicts images and graphs showing successful labeling of SH-SYSY human neuroblastoma cells or neurons derived from induced pluripotent cells (iPSCs) obtained from a subject with a Presenilin mutation (PSmt)) and a control. (A) Schematic diagram illustrating the work flow of an in vitro tau SILK experiment. SH-SY5Y cells and iPSC neurons (far left: micrograph and illustration, respectively) are labeled with 50% $^{13}C_6$ leucine labeled media for 6 days (middle panel, top). Media and cell lysate were sampled daily for twelve days (middle panel, bottom). Finally, labeled and unlabeled tau was immunoprecipitated from each sample using a tau specific antibody, enzymatically digested, and the amount of labeled and unlabeled tau fragment was detected by mass spectrometry. (B) Tau labeling kinetic curve of SH-SY5Y cell lysate and medium. TTR=tracer to trace ratio. (C) Tau labeling kinetic curve of iPSC control (Ctrl) and Presenilin mutation (PSmt) cells. TTR=tracer to trace ratio.
Figure 1A:
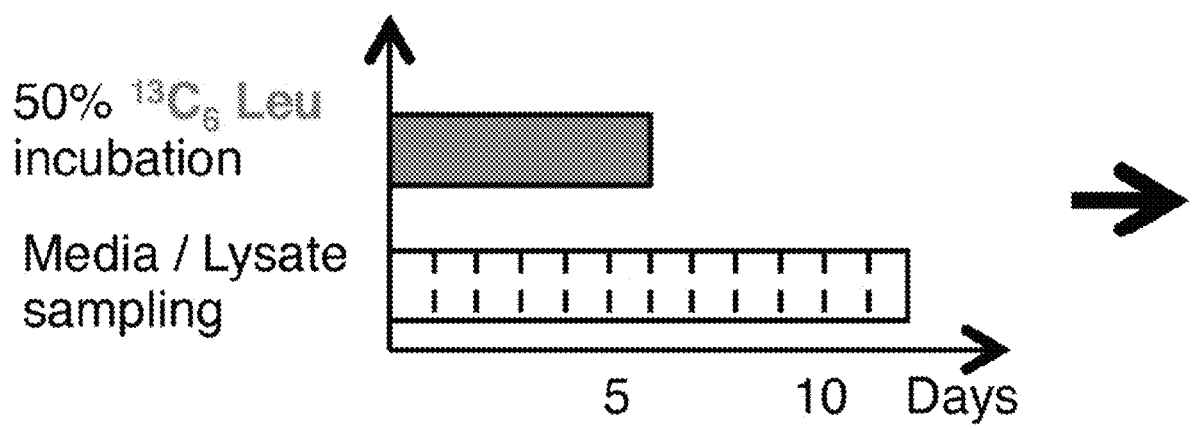
Figure 1A:
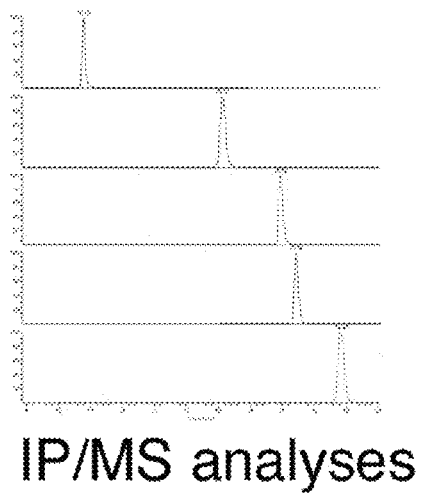

The present invention encompasses methods for determining the kinetics of tau metabolism in the central nervous system (CNS). By using a method of the invention, one skilled in the art may be able to study possible changes in the metabolism of tau. The usefulness of this invention will be evident to those of skill in the art, in that one may determine if a treatment regimen alters the metabolism of tau in a subject in need thereof.

I. TAU Proteins

Tau proteins are the product of alternative splicing from a single gene. In many animals, including but not limited to humans, non-human primates, rodents, fish, cattle, frogs, goats, and chicken, the gene is designated MAPT. In animals wherein the gene is not identified as MAPT, a homolog may be identified by methods well known in the art. The terms "tau protein", "tau" and "tau isoform" may be used interchangeably. Tau proteins may or may not be post-translationally modified. For example, it is known in the art that tau may be phosphorylated, ubiquinated, glycosylated, and glycated.

In humans, there are six isoforms of tau that are generated by alternative splicing of exons 2, 3, and 10 of MAPT. The isoforms range in length from 352 to 441 amino acids. Exons 2 and 3 encode 29-amino acid inserts each in the N-terminus (called N), and hence, tau isoforms may be 2N (both inserts), 1N (exon 2 only), or 0N (neither). All human tau isoforms have three repeats of the microtubule binding domain (called R). Inclusion of exon 10 at the C-terminus leads to inclusion of a fourth microtubule binding domain encoded by exon 10. Hence, human tau isoforms may be comprised of four repeats of the microtubule binding domain (exon 10 included) or three repeats of the microtubule binding domain (exon 10 excluded). Accordingly, a tau isoform may be (2N, 3R), (2N, 4R), (1N, 3R), (1N, 4R), (0N, 3R), or (0N, 4R). Alternative splicing of the gene encoding tau similarly occurs in other animals.

Tau can be found in soluble and insoluble compartments, in monomeric and aggregated forms, in ordered or disordered structures, intracellularly and extracellularly, and may be complexed with other proteins or molecules. One aggregated form of tau is an amyloid. An amyloid is a paracrystalline, ordered protein assembly. An amyloid generally has a cross-beta structure, in vivo or in vitro. Most, but not all, cross-beta structures may be identified by apple-green birefringence when stained with Congo Red and seen under polarized light, or by X-ray fiber diffraction patterns. Amyloid may be located in the periphery or in the central nervous system, or both. Amyloids are well known in the art. See, for example, Eisenberg et al. Cell. 2012 March 16; 148(6):1188-203.

An amyloid may or may not be disease associated. An amyloid may also be associated with more than one disease. The term "amyloidosis" refers to the deposition of amyloid in a subject. The term "tau amyloidosis", therefore, refers to the deposition of tau amyloid in a subject. Tau amyloidosis may be clinically defined by methods known in the art. For example, evidence of tau deposition in the brain may be assessed by using an imaging agent that selectively targets tau aggregates (e.g. a PET, SPECT or MRI imaging agent). See for example, Zhang et al. J Alzheimer's Disease 31(3): 601-612, 2012. Another example includes the T-807 tracer commercially available from Avid.

Subjects with tau amyloidosis are also at an increased risk of developing a disease associated with tau amyloidosis. A disease associated with tau amyloidosis may be referred to as a "tauopathy". Tauopathies known in the art include, but are not limited to, progressive supranuclear palsy, dementia pugilistica, chronic traumatic encephalopathy, frontotemporal dementia and parkinsonism linked to chromosome 17, Lytico-Bodig disease, Parkinson-dementia complex of Guam, tangle-predominant dementia, ganglioglioma and gangliocytoma, meningioangiomatosis, subacute sclerosing panencephalitis, lead encephalopathy, tuberous sclerosis, Hallervorden-Spatz disease, lipofuscinosis, Pick's disease, corticobasal degeneration, argyrophilic grain disease (AGD), Frontotemporal lobar degeneration, Alzheimer's Disease, and frontotemporal dementia.

II. Methods for Measuring the In Vivo Metabolism of Neurally Derived Biomolecules The present invention provides in vitro methods for measuring the in vivo metabolism of tau in a subject. "Tau metabolism" refers to any combination of the synthesis, transport, breakdown, modification, or clearance rate of tau. Tau metabolism may be measured by detecting the amount of labeled tau and unlabeled tau in one or more biological samples obtained from a subject who has received a labeled moiety, and determining the ratio of labeled tau to unlabeled tau in the biological sample. Generally, the ratio of labeled tau to unlabeled tau in the biological sample is directly proportional to the metabolism of tau in the CNS. These measurements may also be used to calculate one or more parameters of tau metabolism. In particular, the present invention provides the critical timeframes at which to obtain one or more biological sample in order to measure the kinetics of tau labeling.

(a) Subject

The present invention provides methods for measuring the in vivo metabolism of tau, i.e. the metabolism of tau in a subject. As used herein, the term "subject" refers to a mammal. Suitable subjects include, but are not limited to a human, a companion animal, a livestock animal, a zoo animal, or a research animal. Non-limiting examples of companion animals include a dog or a cat. Non-limiting example of a livestock animal include a cow, a pig, a horse, a sheep or a goat. Non-limiting examples of a research animal include a non-human primate or a rodent. In preferred embodiments, a subject is a human.

Those of skill in the art will appreciate that while the method of the invention may be used to characterize tau metabolism in a subject with tau amyloidosis, the invention is not limited to subjects with tau amyloidosis. It is envisioned that the method of the invention may be used to characterize tau metabolism in a subject with any disease, disorder, or process, including any disease, disorder or process where altered tau metabolism is known or believed to contribute to the clinical signs or symptoms of the disease, disorder or process. In addition, it is envisioned that the method of the invention may be used to characterize normal tau metabolism in healthy subjects. In some embodiments, a subject is a subject without tau amyloidosis, wherein the subject has no dementia, mild dementia, moderate dementia or severe dementia. In some embodiments, a subject is a subject with tau amyloidosis, wherein the subject has no dementia, mild dementia, moderate dementia or severe dementia. In certain embodiments, the dementia is of a type selected from the group consisting of dementia of the Alzheimer's type, vascular dementia, dementia with Lewy bodies, mixed dementia, dementia of Parkinson's disease type, and frontotemporal dementia. In some embodiments, a subject is a subject without tau amyloidosis, wherein the subject has no dementia, mild dementia, moderate dementia or severe dementia. In certain embodiments, the dementia is of a type selected from the group consisting of dementia of the Alzheimer's type, vascular dementia, dementia with Lewy bodies, mixed dementia, dementia of Parkinson's disease type, and frontotemporal dementia. Any suitable assessment scale for making a diagnosis of dementia may be used.

(b) Labeled Moiety

Tau metabolism is measured in a subject who has received a labeled moiety, preferably a labeled amino acid. Several different moieties may be used to label tau. Generally speaking, the two types of labeling moieties typically utilized in the method of the invention are radioactive isotopes and non-radioactive (stable) isotopes. In a preferred embodiment, non-radioactive isotopes may be used and measured by mass spectrometry. Preferred stable isotopes include deuterium $^2H$, $^{13}C$, $^{15}N$, $^{17 \text{ or } 18}O$, $^{33, 34, \text{ or } 36}S$, but it is recognized that a number of other stable isotope that change the mass of an atom by more or less neutrons than is seen in the prevalent native form would also be effective. A suitable label generally will change the mass of tau under study such that it can be detected in a mass spectrometer. In one embodiment, the labeled moiety is an amino acid comprising a non-radioactive isotope and the amount of labeled tau is measured by mass spectrometry. In preferred embodiments, the non-radioactive isotope is $^{13}C$. In another embodiment, a radioactive isotope may be used, and the amount of labeled tau may be measured with a scintillation counter. One or more labeled moieties may be used simultaneously or in sequence.

Those of skill in the art will appreciate that several labeled amino acids may be used to label tau. Generally, the choice of amino acid is based on a variety of factors such as: (1) The amino acid generally is present in at least one residue of the protein or peptide of interest; (2) The amino acid is generally able to quickly reach the site of protein synthesis and, for proteins synthesized in the CNS, rapidly equilibrate across the blood-brain barrier; (3) The amino acid ideally may be an essential amino acid (not produced by the body), so that a higher percent of labeling may be achieved (Non-essential amino acids may also be used; however, measurements will likely be less accurate); (4) The amino acid label at the selected dose generally does not influence the metabolism of the protein of interest; and (5) availability of the desired amino acid (i.e., some amino acids are much more expensive or harder to manufacture than others). Leucine and phenylalanine are preferred amino acids to label proteins that are synthesized in the CNS. In one embodiment, $^{13}C_6$-phenylalanine is used to label tau. In another embodiment, $^{13}C_6$-leucine is used to label tau.

There are numerous commercial sources of labeled amino acids, both non-radioactive isotopes and radioactive isotopes. Generally, the labeled amino acids may be produced either biologically or synthetically. Biologically produced amino acids may be obtained from an organism (e.g., kelp/seaweed) grown in an enriched mixture of $^{13}C$, $^{15}N$, or another isotope that is incorporated into amino acids as the organism produces proteins. The amino acids are then separated and purified. Alternatively, amino acids may be made with known synthetic chemical processes.

(c) Administration of the Labeled Moiety

A labeled moiety may be administered to a subject by several methods. Suitable methods of administration include intravenously, intra-arterially, subcutaneously, intraperitoneally, intramuscularly, or orally. In a preferred embodiment, a labeled moiety is a labeled amino acid, and the labeled amino acid is administered by intravenous infusion. In another embodiment, a labeled moiety is a labeled amino acid, and the labeled amino acid is administered orally.

The amount (or dose) of labeled moiety can and will vary, as can the duration and frequency of administration. A labeled moiety may be administered to a subject one or more times a day (e.g. 1, 2, 3, 4, 5 or more times a day) on one or more days (e.g. 1, 2, 3, 4, 5, 6, 7, 8, 9, 10 or more days). In each instance, a labeled moiety may be administered slowly over a period of time or as a large single dose. A labeled moiety should be administered in a sufficient amount and for a sufficient duration so that labeled tau is present in the biological sample in an amount that may be reliably quantified. In all instances, "day 0" refers to the first day of labeling, "day 1" refers to The amount of labeled tau is dependent upon (and estimated by) the percentage of label administered and the duration of labeling. Generally speaking, the amount of labeled tau will approximately equal the percentage of label administered multiplied by the duration of labeling. Stated another way, the amount of time of labeling is inversely related to the percent of the label amino acid compared to unlabeled amino acid (e.g. 10%, 50% or 100%). With less time labeling, more amount of labeled amino acid is required to achieve the same amount of tau labeling. Due to the slow turnover rate of tau, a highly sensitive quantification method of labeled tau (e.g. <5%) and/or a long duration of labeling (e.g. >9 hours) are typically required.

The labeling time sufficient for reliable quantification of labeled tau may vary depending upon the biological sample. For example, the labeling time needed when using a blood sample may be less than the required time for reliable quantification of the same tau isoform in a CSF sample.

The amount of labeled tau needed for reliable quantification is a function of the sensitivity of the quantitation method. Current mass spectrometry methods can measure as low as approximately 0.01-0.2% labeled tau, though about 1 to about 2% labeled tau is preferred. However, these measurements are likely to improve (i.e. lower levels of labeled tau may be measured) with advances in technology. One skilled in the art will appreciate that the percent labeled tau needed for reliable quantification via other detection methods can readily be determined by routine experimentation, and labeling protocols can be modified based on the teachings herein.

In some embodiments, labeled amino acid may be intravenously or orally administered to a subject on one or more days. For example, labeled amino acid may be administered on 1, 2, 3, 4, 5, 6, 7, 8, 9, 10, or more days. The total daily dose of labeled amino acid may be divided into multiple smaller doses that are administered sequentially with little time elapsing between each dose, or the multiple doses may be administered at regular or irregular intervals throughout the day. The amount of time that elapses between each dose may be a few seconds, a few minutes, or a few hours. When administered intravenously, a dose of labeled amino acid may be administered over a duration of minutes to hours, including, but not limited to, for at least 10 minutes, at least 20 minutes, at least 30 minutes, at least 1.0 hour, at least 1.5 hours, at least 2.0 hours, at least 2.5 hours, at least 3.0 hours, at least 3.5 hours, at least 4.0 hours, at least 4.5 hours, at least 5.0 hours, at least 5.5 hours, at least 6.0 hours, at least 6.5 hours, at least 7.0 hours, at least 7.5 hours, at least 8.0 hours, at least 8.5 hours, at least 9.0 hours, at least 9.5 hours, at least 10.0 hours, at least 10.5 hours, at least 11.0 hours, at least 11.5 hours, or at least 12 hours. In another aspect, a dose of the labeled amino acid may be intravenously administered over a duration of about 1 hour to about 12 hours, or about 3 hours to about 15 hours. In another aspect, a dose of labeled amino acid may be intravenously administered over a duration of about 1 hours to about 6 hours, about 6 hours to about 12 hours, or about 9 hours to about 15 hours. In another aspect, a dose of intravenously labeled amino acid may be administered over a duration of about 10 minutes to about 30 minutes, about 10 minutes to about 1 hour, or about 30 minute to about 3 hours. In another aspect, a dose of labeled amino acid may be intravenously administered over a duration of about 1 hour to about 3 hours, about 3 hours to about 6 hours, about 6 hours to about 9 hours. In another aspect, a dose of labeled amino acid may be intravenously administered for about 9 hours to about 12 hours, about 10 hours to about 13 hours, or about 12 hours to about 15 hours. When administered orally, each dose of labeled amino acid may be administered as a single dose or multiple doses on one or more day. The multiple oral doses may be administered sequentially or an amount of time may elapse between each dose. The amount of time that elapses between each oral dose may be a few seconds, a few minutes, or a few hours. In a preferred embodiment, when labeled amino acid is administered orally, it is provided to a subject as a drink. In an exemplary embodiment, labeled amino acid may be administered for at least 9 hours, at least 10 hours, at least 11 hours, at least 12 hours or more at 20% to detect labeled tau. In another exemplary embodiment, labeled amino acid may be administered at a daily for 5, 6, 7, 8, 9 or 10 days at about 3% to about 4% labeled amino acid per day.

Those of skill in the art will appreciate that more than one label may be used in a single subject. This would allow multiple labeling of the same biomolecule and may provide information on the production or clearance of that biomolecule at different times. For example, a first label may be given to subject over an initial time period, followed by a pharmacologic agent (drug), and then a second label may be administered. In general, analysis of the samples obtained from this subject would provide a measurement of metabolism before AND after drug administration, directly measuring the pharmacodynamic effect of the drug in the same subject.

Alternatively, multiple labels may be used at the same time to increase labeling of the biomolecule, as well as obtain labeling of a broader range of biomolecules.

(d) Biological Sample

The labeled tau to be measured is in a biological sample obtained from a subject. Suitable biological samples include, but are not limited to, bodily fluids or tissues in which labeled tau may be detected. For instance, in some embodiments, the biological sample is cerebral spinal fluid (CSF). In other embodiments, the biological sample is interstitial fluid (ISF). In still other embodiments, the biological sample is a blood sample. As used herein, "blood" refers to whole blood, blood plasma or blood serum. In another embodiment, the biological sample is a tissue sample. Suitable tissue sample include, but are not limited to, brain tissue and spinal cord tissue.

Cerebrospinal fluid may be obtained by lumbar puncture with or without an indwelling CSF catheter. Blood may be collected by veni-puncture with or without an intravenous catheter, or by a finger stick (or the equivalent thereof), and processed according to methods known in the art. Other types of samples may be collected by direct collection using standard good manufacturing practice (GMP) methods. Biological samples may be used immediately or may be frozen and stored indefinitely.

A first biological sample may be taken from the subject prior to administration of the label to provide a baseline for the subject. Alternatively, when a first biological sample is not taken from the subject prior to administration of the label, an assumption can be made that the baseline sample has a normal isotopic distribution. After administration of the label, one or more samples may be obtained from the subject. Biological samples may be taken over the course of more than two, three, four, five, six, seven, eight, nine, or ten days. Alternatively, biological samples may be collected over the course of at least 2, 3, 4, 5, 6, 7, 8, 9, 10, 11, or 12 weeks. In all instances, "day 0" refers to the first day of labeling, which may or not be the first day of sample collection. In general, biological samples obtained during the labeling phase may be used to determine the rate of synthesis of tau, and blood samples taken during the clearance phase may be used to determine the clearance rate of tau. In addition, biological samples obtained at various times throughout the tau labeling curve may be used to determine other aspects of tau metabolism (e.g. labeled tau peak time, labeled tau peak amount, absolute quantitation, relative labeling, fractional turnover rate). As will be appreciated by those of skill in the art, the number and timing of samples generally may depend upon a number of factors such as: the type of analysis, length of labeling phase, the tau protein of interest, the biological sample, the type of detection, the subject, etc.

The kinetic curve of tau labeling may be affected by the length of the labeling phase, although the kinetics of tau (e.g. production, clearance, turnover rates) will not substantially change. As shown in the Examples, labeled tau peaks earlier and lower following 5 days of labeling compared to 10 days of labeling. Similarly, labeled tau would peak later and higher following labeling for greater than 10 days compared to 10 days of labeling. However, among a similar group of subjects (e.g. matched by age and/or disease status), the shape of the curve will generally be the same. Accordingly, one skilled in the art would be able to use the data provided herein to select a suitable sampling timeframe based on the labeling protocol.

The kinetics of tau metabolism may also differ between types of biological samples. For example, the kinetics of tau metabolism measured in blood samples are expected to be faster than the kinetics measured in CSF samples. For example, the kinetics of tau metabolism measured in bloods samples as compared to CSF samples may be about 2 to about 15 times faster, or about 5 to about 10 times faster.

In some embodiments, a biological sample is a CSF sample or a blood sample and at least 1, 2, 3, 4, 5, 6, 7, 8, 9, or 10 samples are collected between day 0 and day 20, between day 1 and day 20, or between day 2 and day 20. For example, at least 1, 2, 3, 4, 5, 6, 7, 8, 9, or 10 CSF samples may be collected on day 0, 1, 2, 3, 4, 5, 6, 7, 8, 9, 10, 11, 12, 13, 14, 15, 16, 17, 18, 19, or day 20, or any combination thereof. In other embodiments, a biological sample is a CSF sample and at least 1, 2, 3, 4, 5, 6, 7, 8, 9, or 10 samples are collected between day 0 and day 20, between day 1 and day 20, or between day 2 and day 20. In other embodiments, a biological sample is a CSF sample and at least 1, 2, 3, 4, 5, 6, 7, 8, 9, or 10 samples are collected between day 0 and day 15, between day 1 and day 15, between day 2 and day 15. In other embodiments, a biological sample is a CSF sample and at least 1, 2, 3, 4, 5, 6, 7, 8, 9, or 10 samples are collected between day 0 and day 10, between day 1 and day 10, or between day 2 and day 10. In other embodiments, a biological sample is a CSF sample and at least 1, 2, 3, 4, 5, 6, 7, 8, 9, or 10 samples are collected between day 5 and day 20, or between day 5 and day 15. In embodiments where the biological sample is a CSF sample, sample collection between day 0 and day 20 may be used to determine the rate of labeled tau production or metabolic parameters associated with tau production. In embodiments where the biological sample is a blood sample, labeled tau production will likely occur in a shorter timeframe compared to labeled tau production in the CSF.

In some embodiments, a biological sample is a CSF sample or a blood sample and at least 1, 2, 3, 4, 5, 6, 7, 8, 9, or 10 samples are collected between day 20 and day 40. For example, at least 1, 2, 3, 4, 5, 6, 7, 8, 9, or 10 CSF samples may be collected on day 20, 21, 22, 23, 24, 25, 26, 27, 28, 29, 30, 31, 32, 33, 34, 35, 36, 37, 38, 39, or day 40, or any combination thereof. In other embodiments, a biological sample is a CSF sample and at least 1, 2, 3, 4, 5, 6, 7, 8, 9, or 10 samples are collected between day 20 and day 35, between day 20 and day 30, or between day 20 and day 25. In other embodiments, a biological sample is a CSF sample and at least 1, 2, 3, 4, 5, 6, 7, 8, 9, or 10 samples are collected between day 25 and day 40, between day 25 and day 35, or between day 25 and day 30. In embodiments where the biological sample is a CSF sample, sample collection between day 20 and day 40 may be used to determine the peak of labeled tau production or metabolic parameters associated labeled tau peak production (e.g. time to peak, peak height, etc.). In embodiments where the biological sample is a blood sample, the peak of labeled tau production will likely occur earlier than in the CSF. When the peak of labeled tau production is reasonably known, sample collection between day 20 and day 40 may be also used to determine metabolic parameters associated with labeled tau production and labeled tau clearance (e.g. samples collected before the peak of labeled tau production may be used to calculate metabolic parameters associated with labeled tau production and samples collected after the peak of labeled tau production may be used to calculate metabolic parameters associated with labeled tau clearance.)

In some embodiments, a biological sample is a CSF sample or a blood sample and at least 1, 2, 3, 4, 5, 6, 7, 8, 9, or 10 samples are collected between day 25 and day 45. For example, at least 1, 2, 3, 4, 5, 6, 7, 8, 9, or 10 CSF samples may be collected on day 25, 26, 27, 28, 29, 30, 31, 32, 33, 34, 35, 36, 37, 38, 39, 40, 41, 42, 43, 44, or day 45, or any combination thereof. In other embodiments, a biological sample is a CSF sample and at least 1, 2, 3, 4, 5, 6, 7, 8, 9, or 10 samples are collected between day 25 and day 40, between day 25 and day 35, or between day 25 and day 30. In other embodiments, a biological sample is a CSF sample and at least 1, 2, 3, 4, 5, 6, 7, 8, 9, or 10 samples are collected between day 30 and day 45, between day 30 and day 40, or between day 30 and day 35. In embodiments where the biological sample is a CSF sample, sample collection between day 20 and day 40 may be used to determine the peak of labeled tau production or metabolic parameters associated labeled tau peak production (e.g. time to peak, peak height, etc.). In embodiments where the biological sample is a blood sample, the peak of labeled tau production will likely occur earlier than in the CSF. When the peak of labeled tau production is reasonably known, sample collection between day 25 and day 45 may be also used to determine metabolic parameters associated with labeled tau production and labeled tau clearance (e.g. samples collected before the peak of labeled tau production may be used to calculate metabolic parameters associated with labeled tau production and samples collected after the peak of labeled tau production may be used to calculate metabolic parameters associated with labeled tau clearance.)

In some embodiments, a biological sample is a CSF sample or a blood sample and at least 1, 2, 3, 4, 5, 6, 7, 8, 9, or 10 samples are collected between day 40 and day 100. For example, at least 1, 2, 3, 4, 5, 6, 7, 8, 9, or 10 CSF samples may be collected on day 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or day 100. In some embodiments, a biological sample is a CSF sample and at least 1, 2, 3, 4, 5, 6, 7, 8, 9, or 10 samples are collected between day 40 and day 90, between day 40 and day 80, between day 40 and day 70, or between day 40 and day 60. In other embodiments, a biological sample is a CSF sample and at least 1, 2, 3, 4, 5, 6, 7, 8, 9, or 10 samples are collected between day 50 and day 100, between day 50 and day 90, between day 50 and day 80, between day 50 and day 70, or between day 50 and day 60. In yet other embodiments, a biological sample is a CSF sample and at least 1, 2, 3, 4, 5, 6, 7, 8, 9, or 10 samples are collected between day 60 and day 100, between day 60 and day 90, between day 60 and day 85, between day 60 and day 80, or between day 60 and day 70. In still other embodiments, a biological sample is a CSF sample and at least 1, 2, 3, 4, 5, 6, 7, 8, 9, or 10 samples are collected between day 70 and day 100, between day 70 and day 95, between day 70 and day 90, between day 70 and day 85, or between day 70 and day 80. In embodiments where the biological sample is a CSF sample, sample collection between day 40 and day 100 may be used to determine the rate of labeled tau production or metabolic parameters associated with tau production. In embodiments where the biological sample is a blood sample, labeled tau clearance will likely begin earlier and complete sooner than in the CSF.

(e) Detecting the Amount of Labeled Tau and Unlabeled Tau

Suitable methods for the detection of labeled and unlabeled tau can and will vary according to the form of tau under study and/or the type of labeled moiety used to label tau. If the labeled moiety is a radioactively labeled amino acid, then method of detection may be a scintillation counter. If the labeled moiety is a non-radioactively labeled amino acid, then the method of detection typically should be sensitive enough to detect changes in mass of the labeled protein with respect to the unlabeled protein. In a preferred embodiment, mass spectrometry is used to detect differences in mass between the labeled and unlabeled tau. In certain embodiments, gas chromatography mass spectrometry is used. In alternate embodiments, MALDI-TOF mass spectrometry is used. In a preferred embodiment, high-resolution tandem mass spectrometry is used.

Additional techniques may be utilized to separate labeled and unlabeled tau from other proteins and biomolecules in the biological sample prior to detection. As an example, immunoprecipitation may be used to isolate and partially or completely purify tau (including fragments thereof) before it is analyzed by mass spectrometry. Other methods of separating or concentrating tau protein may be used alone or in combination with immunoprecipitation. For example, chromatography techniques may be used to separate tau protein (or fragments thereof) by size, hydrophobicity or affinity. In particular, techniques linking a chromatographic step with mass spectrometry may be used. In an exemplary embodiment, tau is immunoprecipitated and then analyzed by a liquid chromatography system interfaced with a high-resolution tandem MS unit. In another exemplary embodiment, tau is immunoprecipitated and then analyzed by a liquid chromatography system interfaced with a high-resolution tandem MS unit equipped with an electrospray ionization source (LC-ESI-tandem MS).

Labeled and unlabeled tau may also be cleaved into smaller peptides prior to detection. For instance, tau may be enzymatically cleaved with a protease to create several small peptides. Suitable proteases include, but are not limited to, trypsin, Lys-N, Lys-C, and Arg-N. In an exemplary embodiment, labeled and unlabeled tau is completely or partially purified from a biological sample, enzymatically cleaved with a protease, and then analyzed by a liquid chromatography system interfaced with a high-resolution tandem MS unit. In another exemplary embodiment, labeled and unlabeled tau is enzymatically cleaved with a protease and completely or partially purified, and then analyzed by a liquid chromatography system interfaced with a high-resolution tandem MS unit. In certain exemplary embodiments, tau is completely or partially purified by immunoprecipitation.

The invention also provides that multiple isoforms of tau in the same biological sample may be measured simultaneously in the same mass spectrometer sample. That is, both the amount of unlabeled and labeled tau may be detected and measured separately or at the same time for multiple tau isoforms. As such, the invention provides a useful method for screening changes in synthesis and clearance of different isoforms on a large scale and provides a sensitive means to detect and measure proteins involved in the underlying pathophysiology.

(f) Metabolism Analysis

Once the amount of labeled and unlabeled tau has been detected, the relative labeling of tau may be calculated. As used herein, "relative labeling" may refer to a ratio of labeled to unlabeled tau or the percent of labeled tau. The amount of labeled tau, unlabeled tau, or the relative labeling of tau may also be used to calculate one or more additional parameters of tau metabolism. Non-limiting examples of suitable metabolic parameters for tau include a fractional synthesis rate, a fractional clearance rate, an absolute synthesis rate, an absolute clearance rate, a fractional turnover rate, a lag time, a half-life, a time to peak height, a peak height, etc. Methods for calculating these parameters are well known in the art, and those of skill in the art will be familiar with the first order kinetic models of labeling that may be used with the method of the invention. In addition, other parameters, such as lag time and isotopic tracer steady state, may be determined and used as measurements of the tau's metabolism and physiology. Also, modeling may be performed on the data to fit a multiple compartment model to estimate transfer between compartments. Of course, the type of mathematical modeling chosen will depend on the individual protein synthetic and clearance parameters (e.g., one-pool, multiple pools, steady state, non-steady-state, compartmental modeling, etc.). Generally, the relative labeling of tau in a biological sample is directly proportional to the metabolism of tau in the CNS. For example, the increase in labeled tau during the production phase and the removal of labeled tau during the clearance phase reflects the relative production and clearance of tau in the CNS. Accordingly, parameters of tau metabolism calculated using measurements of labeled and/or unlabeled tau also reflect the metabolism of tau in the CNS.

The amount of labeled tau in a biological sample at a given time reflects the metabolism of tau, including the synthesis rate (i.e., production) or the clearance rate (i.e., removal or destruction). The invention provides that the synthesis of tau is typically based upon the rate of increase of the labeled/unlabeled protein ratio over time (i.e., the slope, the exponential fit curve, or a compartmental model fit defines the rate of tau synthesis). For these calculations, a minimum of one sample is typically required (one could estimate the baseline label), and two or more samples are preferred to calculate the rate of increase of the label over time. Conversely, after the administration of labeled amino acid is terminated, the rate of decrease of the ratio of labeled to unlabeled protein typically reflects the clearance rate of that protein. For these calculations, a minimum of one sample is typically required (one could estimate the baseline label), and two or more samples are preferred to calculate the rate of decrease of the label from tau over time.

In an exemplary embodiment, as illustrated in the examples, the in vivo metabolism of tau is measured by orally administering $^{13}C_6$-leucine to a subject for 5 or 10 days and collecting at least one biological sample at a time point greater than 2 days after the first administration of the label. The biological sample may be collected from CSF. The amount of labeled and unlabeled tau in the biological samples is typically determined by immunoprecipitation followed by LC-ESI-tandem MS. From these measurements, the amount of labeled tau and unlabeled tau may be determined, and these measurements permits the determination of metabolism parameters of tau kinetics, such as relative labeling, rate of synthesis, rate of clearance of tau.

(g) Preferred Embodiments

A method for measuring the metabolism of tau in a subject, the method comprising: (a) administering, in the form of at least one bolus or at least one infusion, a total daily dose of about 0.1 g to about 10 g of at least one labeled amino acid to the subject for at least three days, at least five days, or least 10 days; (b) collecting at least one biological sample from the subject between day 1 or day 2 and day 20, day 20 and day 40, day 40 and day 100, or a combination thereof; (c) detecting and measuring by mass spectrometry the amount of labeled tau, or the amount of labeled tau and unlabeled tau, in each biological sample; and (d) calculating the metabolism of tau using the measurements from step (c), wherein the amount of labeled tau, optionally expressed as the relative labeling of tau, in the biological sample at a given time reflects the metabolism of tau. Alternatively, the daily dose can be about 0.5 g to about 5 g of labelled amino acid, 0.5 g to about 1 g of labelled amino acid, or about 1 g to about 5 g of labelled amino acid. In each embodiment, the daily dose may be divided into multiple smaller doses that are administered in a single sitting, or at regular or irregular intervals throughout the day. Preferred biological samples include CSF samples, blood samples or combinations thereof. The method may further comprise enzymatically cleaving tau with a protease and/or completely or partially purifying tau or fragments thereof between step (b) and (c).

A method for measuring the metabolism of tau in a subject, the method comprising: (a) administering, in the form of at least one bolus or at least one infusion, at least one labeled amino acid to the subject, wherein the label is administered to the subject on two or more days between day 0 and about day 3, preferably between day 0 and about day 5, more preferably between day 0 and about day 10, as a total daily dose of about 0.1 g to about 10 g; (b) collecting at least one biological sample from the subject between day 1 or day 2 and day 20, day 20 and day 40, day 40 and day 100, or a combination thereof; (c) detecting and measuring by mass spectrometry the amount of labeled tau, or the amount of labeled tau and unlabeled tau, in each biological sample; and (d) calculating the metabolism of tau using the measurements from step (c), wherein the amount of labeled tau, optionally expressed as the relative labeling of tau, in the biological sample at a given time reflects the metabolism of tau. Alternatively, the daily dose can be about 0.5 g to about 5 g of labelled amino acid, 0.5 g to about 1 g of labelled amino acid, or about 1 g to about 5 g of labelled amino acid. Preferred biological samples include CSF samples, blood samples or combinations thereof. The method may further comprise enzymatically cleaving tau with a protease and/or completely or partially purifying tau or fragments thereof between step (b) and (c).

A method for measuring the metabolism of tau in a subject, the method comprising: (a) administering, in the form of at least one bolus or at least one infusion, at least one labeled amino acid to the subject, wherein the label is administered to the subject on 2, 3, 4 or more days between day 0 and about day 5, preferably between day 0 and about day 10, as a total daily dose of about 0.1 g to about 10 g; (b) collecting at least one biological sample from the subject between day 1 or day 2 and day 20, day 20 and day 40, day 40 and day 100, or a combination thereof; (c) detecting and measuring by mass spectrometry the amount of labeled tau, or the amount of labeled tau and unlabeled tau, in each biological sample; and (d) calculating the metabolism of tau using the measurements from step (c), wherein the amount of labeled tau, optionally expressed as the relative labeling of tau, in the biological sample at a given time reflects the metabolism of tau. Alternatively, the daily dose can be about 0.5 g to about 5 g of labelled amino acid, 0.5 g to about 1 g of labelled amino acid, or about 1 g to about 5 g of labelled amino acid. In each embodiment, the daily dose may be divided into multiple smaller doses that are administered in a single sitting, or at regular or irregular intervals throughout the day. Preferred biological samples include CSF samples, blood samples or combinations thereof. The method may further comprise enzymatically cleaving tau with a protease and/or completely or partially purifying tau or fragments thereof between step (b) and (c).

A method for measuring the metabolism of tau in a subject, the method comprising: (a) administering, in the form of at least one bolus or at least one infusion, at least one labeled amino acid to the subject, wherein the label is administered to the subject on 2, 3, 4, 5, 7, 8, or 9 days between day 0 and about day 10, as a total daily dose of about 0.1 g to about 10 g; (b) collecting at least one biological sample from the subject between day 1 or day 2 and day 20, day 20 and day 40, day 40 and day 100, or a combination thereof; (c) detecting and measuring by mass spectrometry the amount of labeled tau, or the amount of labeled tau and unlabeled tau, in each biological sample; and (d) calculating the metabolism of tau using the measurements from step (c), wherein the amount of labeled tau, optionally expressed as the relative labeling of tau, in the biological sample at a given time reflects the metabolism of tau. Alternatively, the daily dose can be about 0.5 g to about 5 g of labelled amino acid, 0.5 g to about 1 g of labelled amino acid, or about 1 g to about 5 g of labelled amino acid. In each embodiment, the daily dose may be divided into multiple smaller doses that are administered in a single sitting, or at regular or irregular intervals throughout the day. Preferred biological samples include CSF samples, blood samples or combinations thereof. The method may further comprise enzymatically cleaving tau with a protease and/or completely or partially purifying tau or fragments thereof between step (b) and (c).

A method for measuring the metabolism of tau in a subject, the method comprising: (a) administering, in the form of at least one bolus or at least one infusion, a total daily dose of about 0.1 g to about 10 g of at least one labeled amino acid to the subject for at least three days, at least five days, or least 10 days; (b) collecting at least one biological sample from the subject based on the calculation: half-life of tau±1, 2, 3, 4, 5, 6, 7, 8, 9, or 10 days from the half-life of tau; (c) detecting and measuring by mass spectrometry the amount of labeled tau, or the amount of labeled tau and unlabeled tau, in each biological sample; and (d) calculating the metabolism of tau using the measurements from step (c), wherein the amount of labeled tau, optionally expressed as the relative labeling of tau, in the biological sample at a given time reflects the metabolism of tau. Alternatively, the daily dose can be about 0.5 g to about 5 g of labelled amino acid, 0.5 g to about 1 g of labelled amino acid, or about 1 g to about 5 g of labelled amino acid. In each embodiment, the daily dose may be divided into multiple smaller doses that are administered in a single sitting, or at regular or irregular intervals throughout the day. Preferred biological samples include CSF samples, blood samples or combinations thereof. The method may further comprise enzymatically cleaving tau with a protease and/or completely or partially purifying tau or fragments thereof between step (b) and (c).

A method for measuring the metabolism of tau in a subject, the method comprising: (a) administering, in the form of at least one bolus or at least one infusion, a total daily dose of about 0.1 g to about 10 g of at least one labeled amino acid to the subject for at least three days, at least five days, or least 10 days; (b) only collecting one or more biological sample from the subject based on the calculation: half-life of tau±1, 2, 3, 4, 5, 6, 7, 8, 9, or 10 days from the half-life of tau (i.e. no samples are collected outside this timeframe); (c) detecting and measuring by mass spectrometry the amount of labeled tau, or the amount of labeled tau and unlabeled tau, in each biological sample; and (d) calculating the metabolism of tau using the measurements from step (c), wherein the amount of labeled tau, optionally expressed as the relative labeling of tau, in the biological sample at a given time reflects the metabolism of tau. Alternatively, the daily dose can be about 0.5 g to about 5 g of labelled amino acid, 0.5 g to about 1 g of labelled amino acid, or about 1 g to about 5 g of labelled amino acid. In each embodiment, the daily dose may be divided into multiple smaller doses that are administered in a single sitting, or at regular or irregular intervals throughout the day. Preferred biological samples include CSF samples, blood samples or combinations thereof. The method may further comprise enzymatically cleaving tau with a protease and/or completely or partially purifying tau or fragments thereof between step (b) and (c).

An in vitro method for measuring the metabolism of tau in a subject, the method comprising (a) detecting and measuring by mass spectrometry the amount of labeled tau, or the amount of labeled tau and unlabeled tau, in each biological sample obtained from the subject; and (b) calculating the metabolism of tau using the amount of labeled, or labeled and unlabeled tau, determined in step (a), wherein the amount of labeled tau, optionally expressed as the relative labeling of tau, in the biological sample at a given time reflects the metabolism of tau; and wherein (i) the label was administered daily as at least one bolus or at least one infusion on day 0 to at least about day 3, preferably day 0 to at least about day 5, more preferably day 0 to at least about day 10, and (ii) each biological sample was collected from the subject between day 1 or day 2 and day 20, day 20 and day 40, day 40 and day 100, or a combination thereof. Alternatively, the daily dose can be about 0.5 g to about 5 g of labelled amino acid, 0.5 g to about 1 g of labelled amino acid, or about 1 g to about 5 g of labelled amino acid. In each embodiment, the daily dose may be divided into multiple smaller doses that are administered in a single sitting, or at regular or irregular intervals throughout the day. Preferred biological samples include CSF samples, blood samples or combinations thereof. The method may further comprise enzymatically cleaving tau with a protease and/or completely or partially purifying tau or fragments thereof between step (a) and (b).

An in vitro method for measuring the metabolism of tau in a subject, the method comprising (a) detecting and measuring by mass spectrometry the amount of labeled tau, or the amount of labeled tau and unlabeled tau, in each biological sample obtained from the subject; and (b) calculating the metabolism of tau using the amount of labeled, or labeled and unlabeled tau, determined in step (a), wherein the amount of labeled tau, optionally expressed as the relative labeling of tau, in the biological sample at a given time reflects the metabolism of tau; and wherein (i) the label was administered as at least one bolus or at least one infusion on two or more days between day 0 and about day 3, preferably between day 0 and about day 5, more preferably between day 0 and about day 10, and (ii) each biological sample was collected from the subject between day 1 or day 2 and day 20, day 20 and day 40, day 40 and day 100, or a combination thereof. Alternatively, the daily dose can be about 0.5 g to about 5 g of labelled amino acid, 0.5 g to about 1 g of labelled amino acid, or about 1 g to about 5 g of labelled amino acid. In each embodiment, the daily dose may be divided into multiple smaller doses that are administered in a single sitting, or at regular or irregular intervals throughout the day. Preferred biological samples include CSF samples, blood samples or combinations thereof. The method may further comprise enzymatically cleaving tau with a protease and/or completely or partially purifying tau or fragments thereof between step (a) and (b).

An in vitro method for measuring the metabolism of tau in a subject, the method comprising (a) detecting and measuring by mass spectrometry the amount of labeled tau, or the amount of labeled tau and unlabeled tau, in each biological sample obtained from the subject; and (b) calculating the metabolism of tau using the amount of labeled, or labeled and unlabeled tau, determined in step (a), wherein the amount of labeled tau, optionally expressed as the relative labeling of tau, in the biological sample at a given time reflects the metabolism of tau; and wherein (i) the label is administered as at least one bolus or at least one infusion to the subject on 2, 3, 4 or more days between day 0 and about day 5, preferably between day 0 and about day 10, and (ii) each biological sample was collected from the subject between day 1 or day 2 and day 20, day 20 and day 40, day 40 and day 100, or a combination thereof. Alternatively, the daily dose can be about 0.5 g to about 5 g of labelled amino acid, 0.5 g to about 1 g of labelled amino acid, or about 1 g to about 5 g of labelled amino acid. In each embodiment, the daily dose may be divided into multiple smaller doses that are administered in a single sitting, or at regular or irregular intervals throughout the day. Preferred biological samples include CSF samples, blood samples or combinations thereof. The method may further comprise enzymatically cleaving tau with a protease and/or completely or partially purifying tau or fragments thereof between step (a) and (b).

An in vitro method for measuring the metabolism of tau in a subject, the method comprising (a) detecting and measuring by mass spectrometry the amount of labeled tau, or the amount of labeled tau and unlabeled tau, in each biological sample obtained from the subject; and (b) calculating the metabolism of tau using the amount of labeled, or labeled and unlabeled tau, determined in step (a), wherein the amount of labeled tau, optionally expressed as the relative labeling of tau, in the biological sample at a given time reflects the metabolism of tau; and wherein (i) the label is administered as at least one bolus or at least one infusion to the subject on 2, 3, 4, 5, 7, 8, or 9 days between day 0 and about day 10, and (ii) each biological sample was collected from the subject between day 1 or day 2 and day 20, day 20 and day 40, day 40 and day 100, or a combination thereof. Alternatively, the daily dose can be about 0.5 g to about 5 g of labelled amino acid, 0.5 g to about 1 g of labelled amino acid, or about 1 g to about 5 g of labelled amino acid. In each embodiment, the daily dose may be divided into multiple smaller doses that are administered in a single sitting, or at regular or irregular intervals throughout the day. Preferred biological samples include CSF samples, blood samples or combinations thereof. The method may further comprise enzymatically cleaving tau with a protease and/or completely or partially purifying tau or fragments thereof between step (a) and (b).

An in vitro method for measuring the metabolism of tau in a subject, the method comprising (a) detecting and measuring by mass spectrometry the amount of labeled tau, or the amount of labeled tau and unlabeled tau, in each biological sample obtained from the subject; and (b) calculating the metabolism of tau using the amount of labeled, or labeled and unlabeled tau, determined in step (a), wherein the amount of labeled tau, optionally expressed as the relative labeling of tau, in the biological sample at a given time reflects the metabolism of tau; and wherein (i) the label was administered daily as at least one bolus or at least one infusion on day 0 to at least about day 3, preferably day 0 to at least about day 5, more preferably day 0 to at least about day 10, and (ii) each biological sample was collected from the subject based on the calculation: half-life of tau$\pm$1, 2, 3, 4, 5, 6, 7, 8, 9, or 10 days from the half-life of tau. Alternatively, the daily dose can be about 0.5 g to about 5 g of labelled amino acid, 0.5 g to about 1 g of labelled amino acid, or about 1 g to about 5 g of labelled amino acid. In each embodiment, the daily dose may be divided into multiple smaller doses that are administered in a single sitting, or at regular or irregular intervals throughout the day. Preferred biological samples include CSF samples, blood samples or combinations thereof. The method may further comprise enzymatically cleaving tau with a protease and/or completely or partially purifying tau or fragments thereof between step (a) and (b).

An in vitro method for measuring the metabolism of tau in a subject, the method comprising (a) detecting and measuring by mass spectrometry the amount of labeled tau, or the amount of labeled tau and unlabeled tau, in each biological sample obtained from the subject; and (b) calculating the metabolism of tau using the amount of labeled, or labeled and unlabeled tau, determined in step (a), wherein the amount of labeled tau, optionally expressed as the relative labeling of tau, in the biological sample at a given time reflects the metabolism of tau; and wherein (i) the label was administered daily as at least one bolus or at least one infusion on day 0 to at least about day 3, preferably day 0 to at least about day 5, more preferably day 0 to at least about day 10, and (ii) each biological sample was only collected from the subject based on the calculation: half-life of tau±1, 2, 3, 4, 5, 6, 7, 8, 9, or 10 days (i.e. no samples are collected outside this timeframe). Alternatively, the daily dose can be about 0.5 g to about 5 g of labelled amino acid, 0.5 g to about 1 g of labelled amino acid, or about 1 g to about 5 g of labelled amino acid. In each embodiment, the daily dose may be divided into multiple smaller doses that are administered in a single sitting, or at regular or irregular intervals throughout the day. Preferred biological samples include CSF samples, blood samples or combinations thereof. The method may further comprise enzymatically cleaving tau with a protease and/or completely or partially purifying tau or fragments thereof between step (a) and (b).

III. Kits for Diagnosing or Monitoring the Progression or Treatment of Neurological and Neurodegenerative Diseases The current invention provides kits for measuring tau or monitoring the progression or treatment of a neurological or neurodegenerative disease associated with tau by measuring the in vivo metabolism of tau in a subject. Generally, a kit comprises a labeled amino acid, means for administering the labeled amino acid, means for collecting biological samples over time, and instructions for detecting and measuring the amount of labeled tau and/or unlabeled tau so that a metabolic parameter may be calculated. The metabolic parameter then may be compared to a metabolic parameter of a normal, healthy individual or compared to a metabolic parameter from the same subject generated at an earlier time. Suitable metabolic parameters are described above. In a preferred embodiment, the kit comprises $^{13}C_6$-leucine or $^{13}C_6$-phenylalanine, the protein to be labeled is tau, and the disease to be assessed is tau amyloidosis.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

"Clearance rate" refers to the rate at which the biomolecule of interest, such as tau, is removed.

"Fractional clearance rate" or FCR is calculated as the natural log of the ratio of labeled biomolecule, such as tau, over a specified period of time.

"Fractional synthesis rate" or FSR is calculated as the slope of the increasing ratio of labeled biomolecule, such as tau, over a specified period of time divided by the predicted value of the labeled precursor.

"Fractional turnover rate" or FTR is that rate of irreversible loss of a biomolecule, such as tau, from the CNS, and is the sum of losses to CSF and other loss pathways (e.g. local tissue uptake, proteolysis, deposition into amyloid).

"Isotope" refers to all forms of a given element whose nuclei have the same atomic number but have different mass numbers because they contain different numbers of neutrons. By way of a non-limiting example, $^{12}C$ and $^{13}C$ are both stable isotopes of carbon.

"Lag time" generally refers to the delay of time from when the biomolecule, such as tau, is first labeled until the labeled biomolecule is detected.

"Metabolism" refers to any combination of the synthesis, transport, breakdown, modification, or clearance rate of a biomolecule, such as tau.

"Neurally derived cells" includes all cells within the blood-brain-barrier including neurons, astrocytes, microglia, choroid plexus cells, ependymal cells, other glial cells, etc.

"Relative labeling" refers to the ratio of labeled tau to unlabeled tau or the percent labeled tau. Relative labeling may be expressed using any suitable unit. As a non-limiting example, the ratio of labeled tau to unlabeled tau may be expressed as a tracer to trace relationship (TTR) obtained from a mass spectrometric analysis. As another non-limiting example, TTR ratios may be converted to mole fraction labeled.

"Start of labeling" refers to the time at which labeling begins, i.e. time=0. For tau labeling protocols that require administration of a label on multiple days, the "start of labeling" refers to the first time label is administered. After the start of labeling, sample collection may begin as soon as labeled tau is reliably detected, which may occur within one or more hour from the start of labeling.

"Steady state" refers to a state during which there is insignificant change in the measured parameter over a specified period of time.

"Synthesis rate" refers to the rate at which the biomolecule of interest is synthesized.

In metabolic tracer studies, a "stable isotope" is a nonradioactive isotope that is less abundant than the most abundant naturally occurring isotope.

"Subject" as used herein means a living organism having a central nervous system. In particular, the subject is a mammal. Suitable subjects include research animals, companion animals, farm animals, and zoo animals. The preferred subject is a human.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Development of Tau Immunoprecipitation (IP) and Mass Spectrometry Methods CSF tau is estimated to be a heterogeneous pool of truncated fragments and is low in abundance. For example, total tau in young normal control is estimated to be approximately 200 pg/mL=4.4 fmol/mL. To achieve high recovery of tau from human CSF, various tau antibodies with epitopes ranging from N-terminus to C-terminus of full length tau were tested for IP efficiencies (Table 1, FIG. 2). Human CSF containing a range of tau (pg to ng) and cell culture media containing picogram to nanogram of tau (SH-SYSY human neuroblastoma and HEK293T cells transiently overexpressing full length tau) were used for the validation assay. Recovery rate was assessed by N-terminus tau ELISA (HJ8.5 capture, HJ8.7-biotin detection) and the three antibodies that recognize the N-terminus of tau (Tau12, HJ8.5, and HJ8.7) had the highest immunoprecipitation efficiencies (on average 99.3%) for CSF tau. This data suggests that full length tau is not present in human CSF, which is consistent with the literature. N-terminal antibody HJ8.5 and mid-domain antibody Tau1 were identified as optimal antibodies for immunoprecipitation of multiple tau species in CSF.

To quantitate tau peptide using mass spectrometry (MS) analyses, immunoprecipitated tau was subsequently digested with 400 ng trypsin for 16 hrs at 37° C. Alternative enzymes and duration of digestion may also be used. Digested samples were desalted or cleaned up using Toptip C18 columns (glygen). Following clean up, samples were dried and resuspended in 2% acetonitrile and 0.1% formic acid and injected for nano LC-MS analyses (Thermoscientific TSQ, or Thermoscientific Orbitrap Fusion). By peptide fingerprinting, we detected multiple fragments from tau in human CSF, SH-SY5Y media (see Example 2), and the media from HEK293T overexpressing human tau, which included peptides that have a single or double leucines such as TPSLPTPPTR (SEQ ID NO: 2) and LQTAPVPMPDLK (SEQ ID NO: 7). TPSLPTPPTR (SEQ ID NO: 2) had the largest and most consistent signal in all the samples and thus used for further analyses of the quantitation of $^{13}C_6$-leucine labeled tau.

Figure 2B:
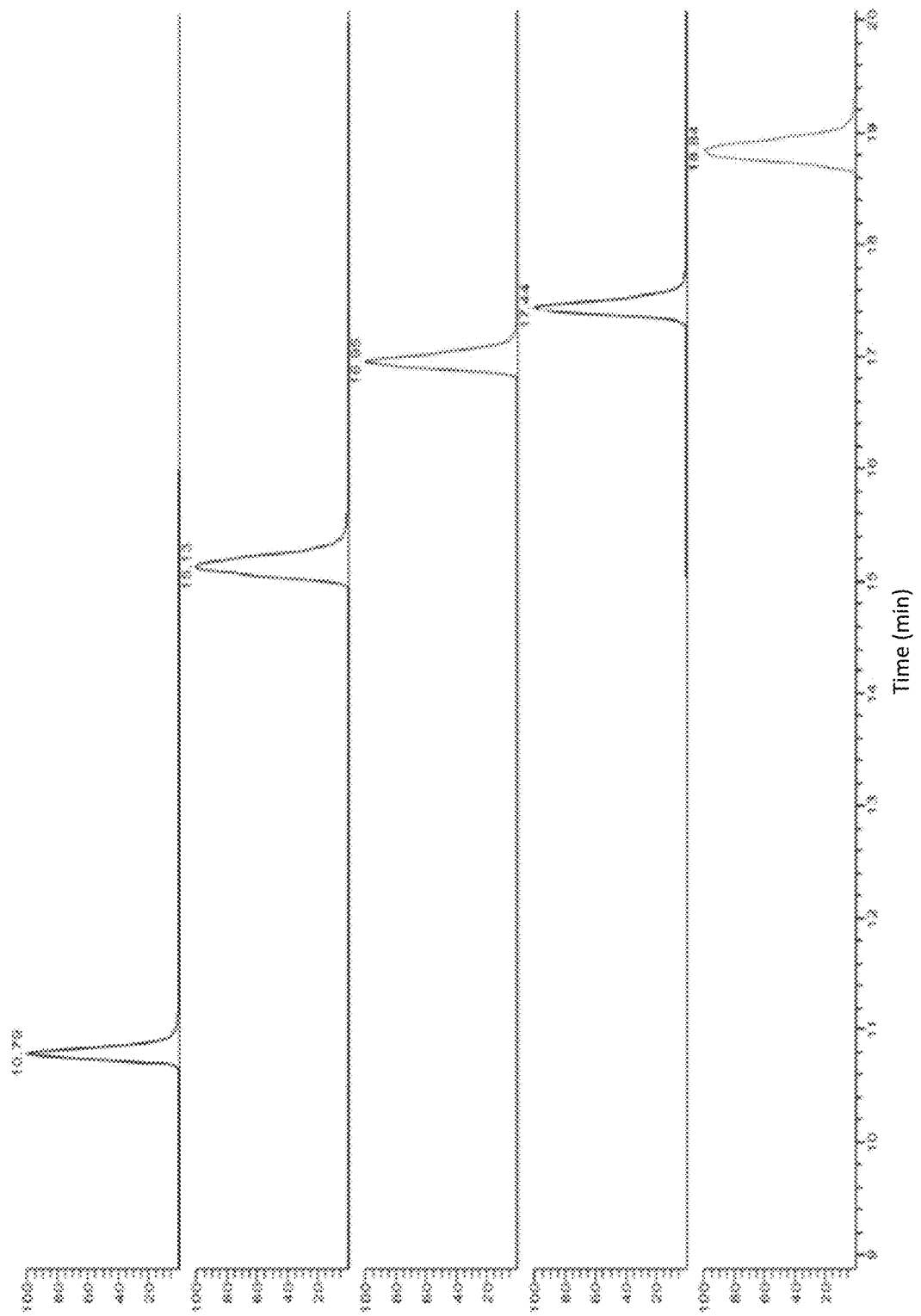
Figure 2C:
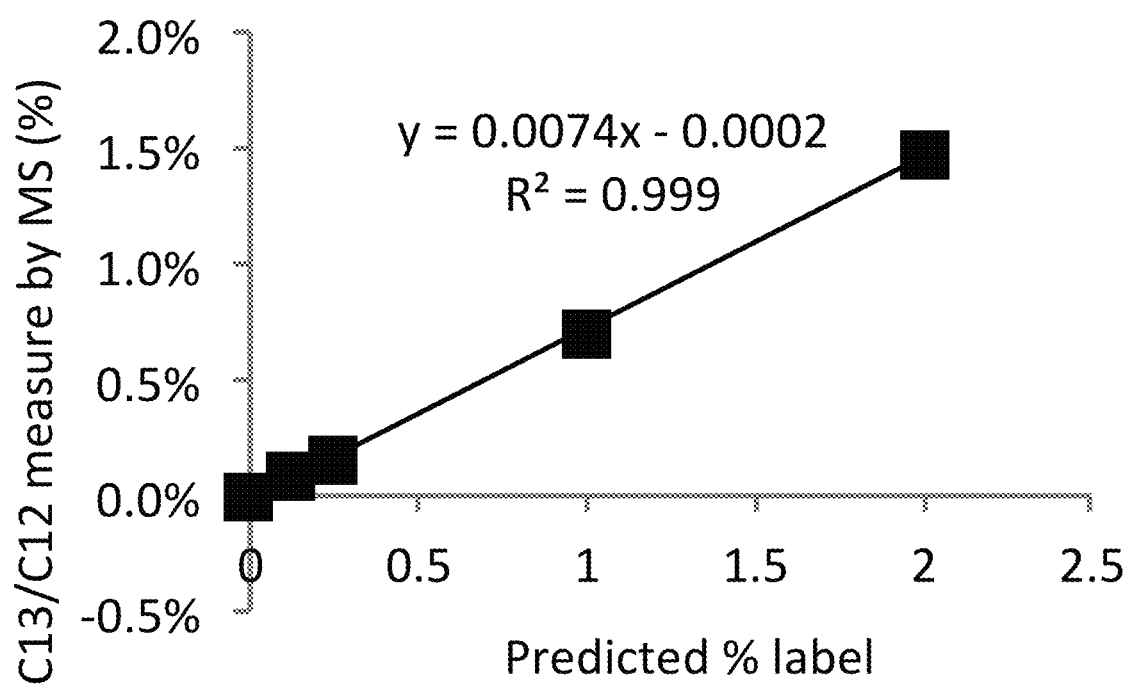
Figure 3A:
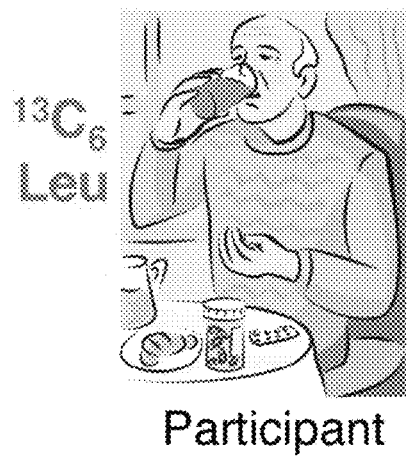
FIG. 3A-D is an illustration providing an overview of one embodiment of the method of the invention. (A) Subjects are orally labeled with a stable isotope labeled amino acid ($^{13}C_6$ leucine). (B) Cerebrospinal fluid (CSF) and blood samples are collected after the start of labeling. (C) Tau is immunoprecipitated from the CSF sample and processed for mass spectrometry analysis. The amount of unlabeled and labeled tau in the sample is determined mass spectrometry. (D) Schematic diagram of isotopic enrichment of tau in CNS (top) and an example of a labeling and sampling timeline (bottom). The increase in labeled tau during the production phase and the removal of labeled tau during the clearance phase reflects the relative production and clearance, respectively, of tau in the central nervous system (CNS).
Figure 3B:
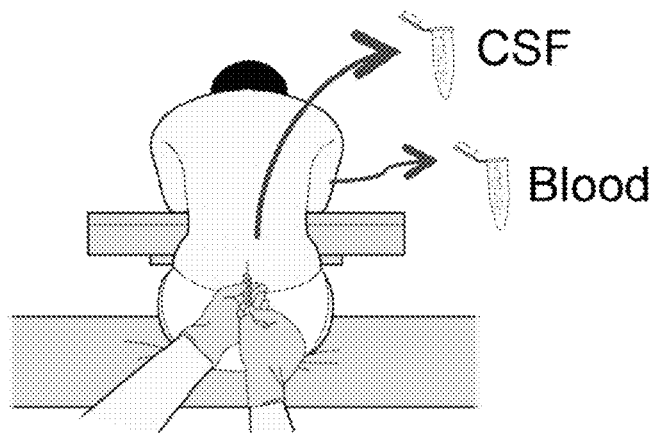
Figure 3C:
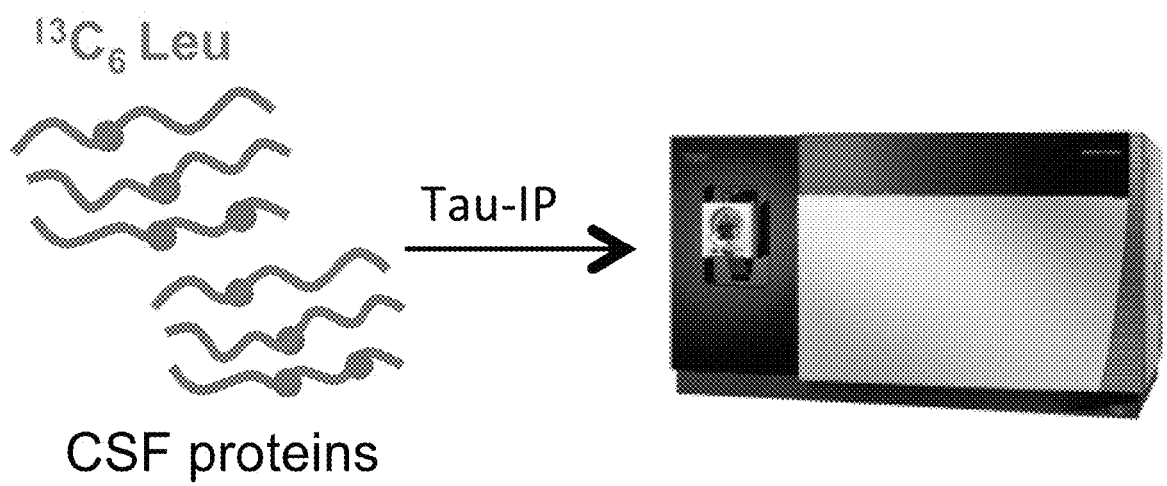
Figure 3D:
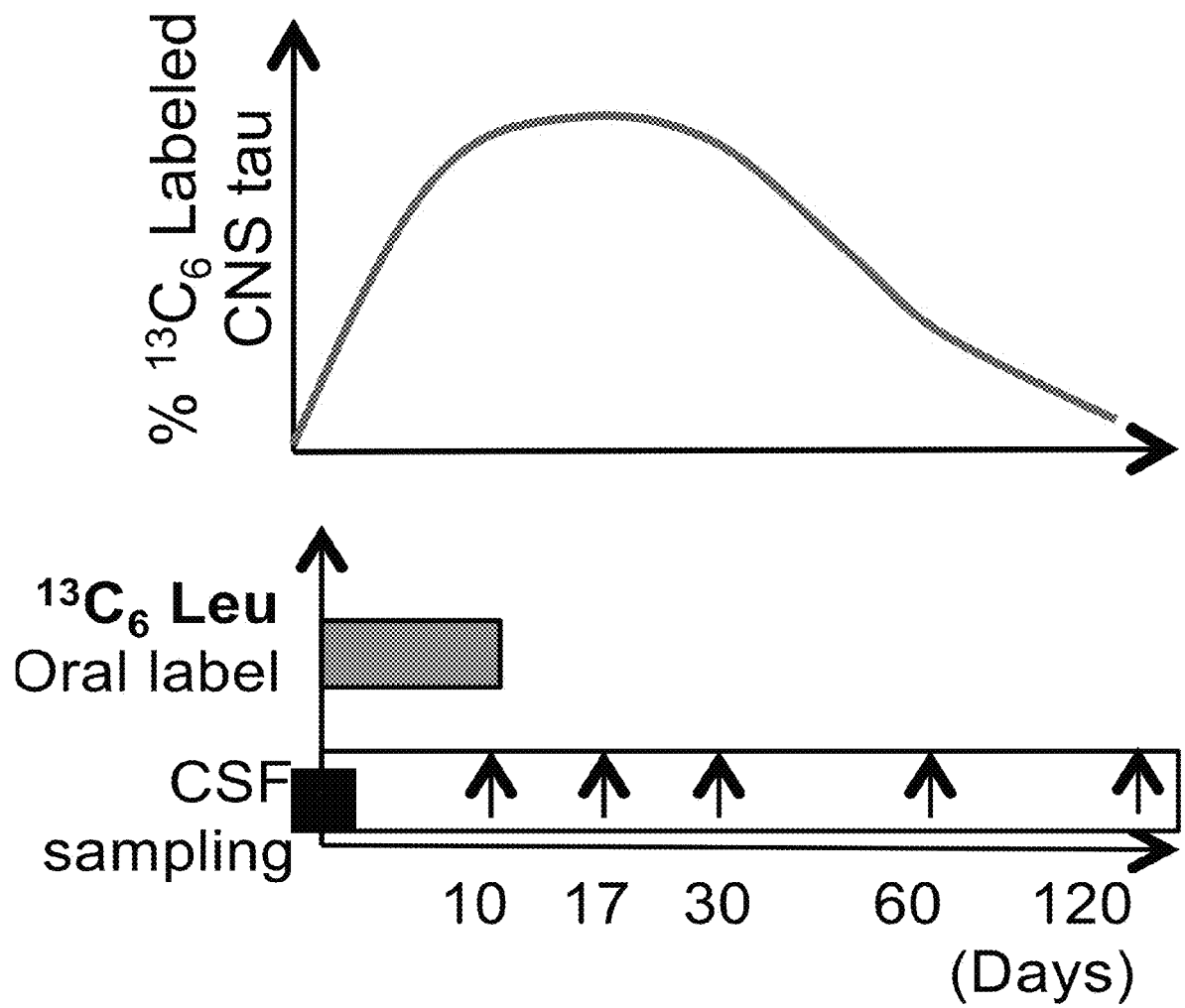
Figure 4A:
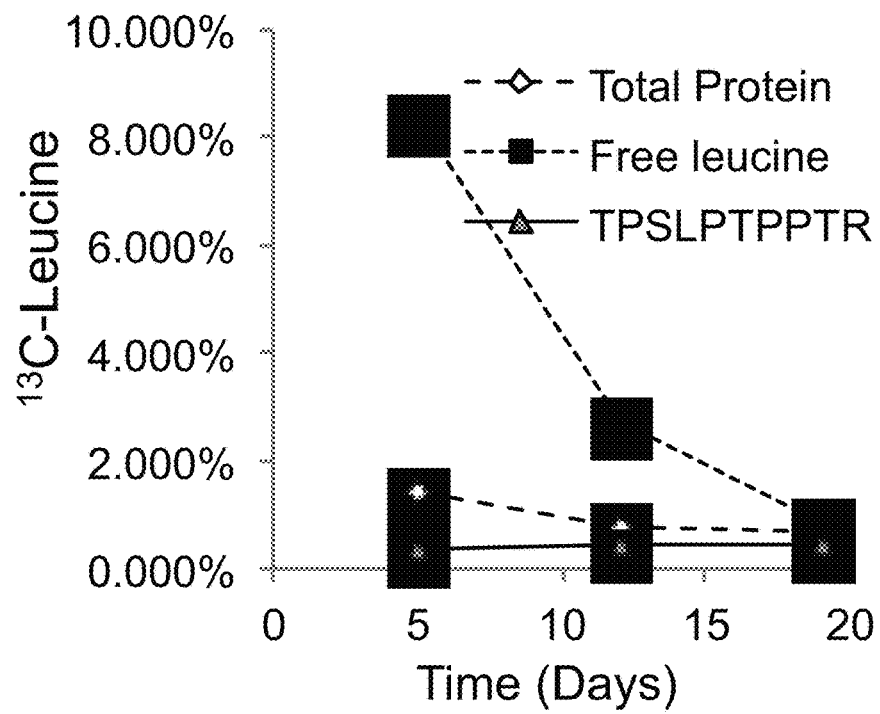
FIG. 4A-F depicts graphs showing successful labeling of tau in vivo and analysis of labeled tau kinetics in vitro. Five young, normal control (NC) subjects were orally administered $^{13}C_6$ leucine for 5 days (NC01) or 10 days (NC02, NC03, NC05, NC06). CSF samples were obtained on days 14 days, 28 days, 42 days, and 67-84. % free leucine and total protein in each CSF sample was measured by GC-MS. Following immunoprecipitation with an anti-tau antibody and tryptic digestion, $^{13}C_6$ leucine-labeled tau and unlabeled tau in each CSF sample were measured using LC-MS. TPSLPTPPTR (SEQ ID NO:2) was used for quantitation of labeled tau. (A) NC01, (B) NC02, (C) NC03, (D) NC05, (E) NC06. In each panel % free leucine (square), total protein (diamond) and tau tryptic peptide TPSLPTPPTR (SEQ ID NO: 2; triangle).
Figure 4B:
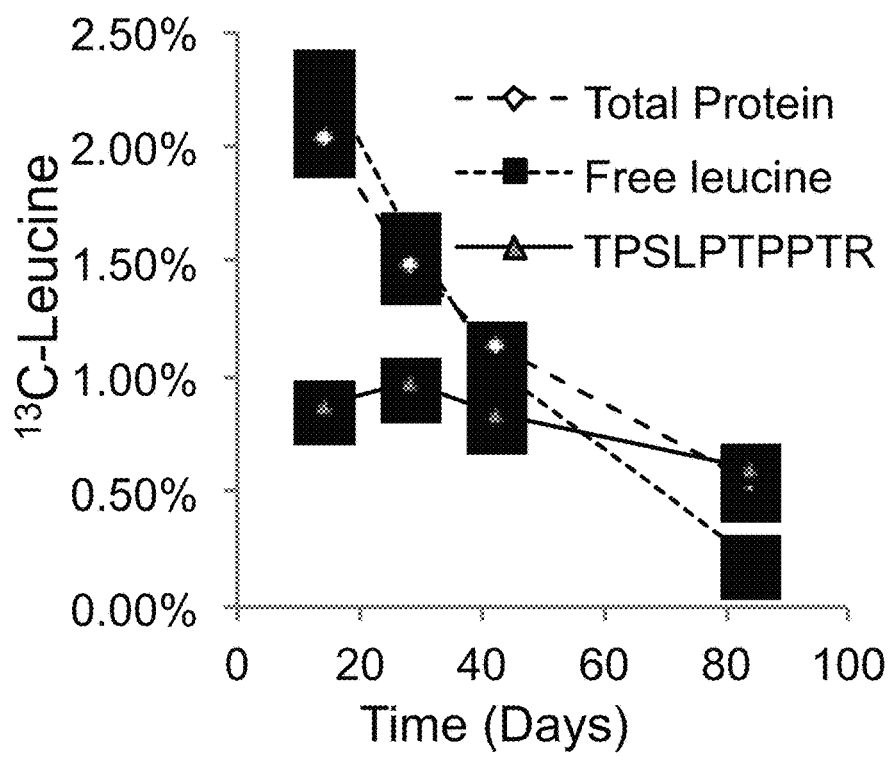
Figure 4C:
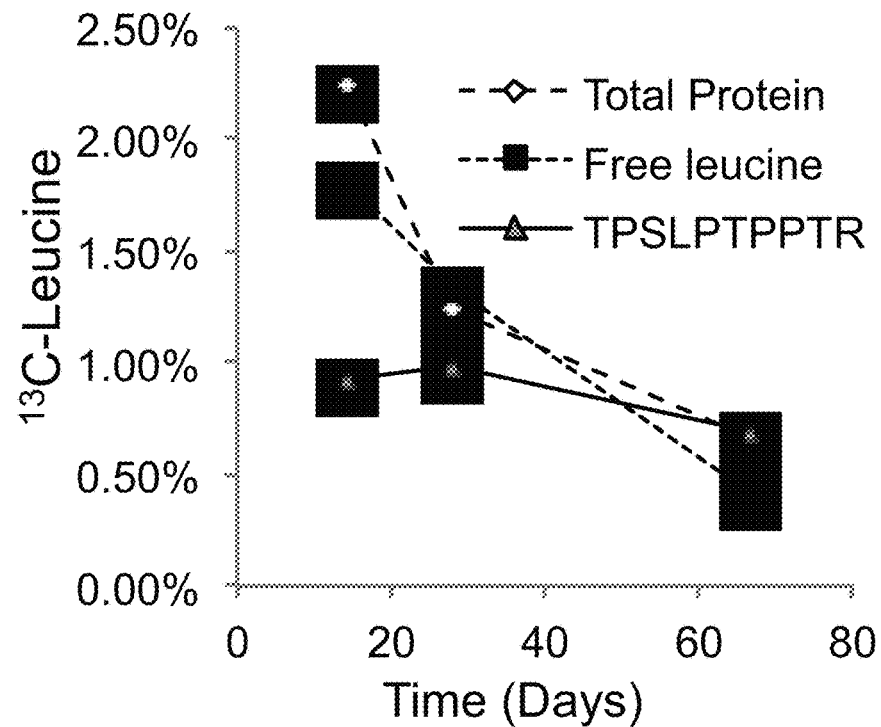
Figure 4D:
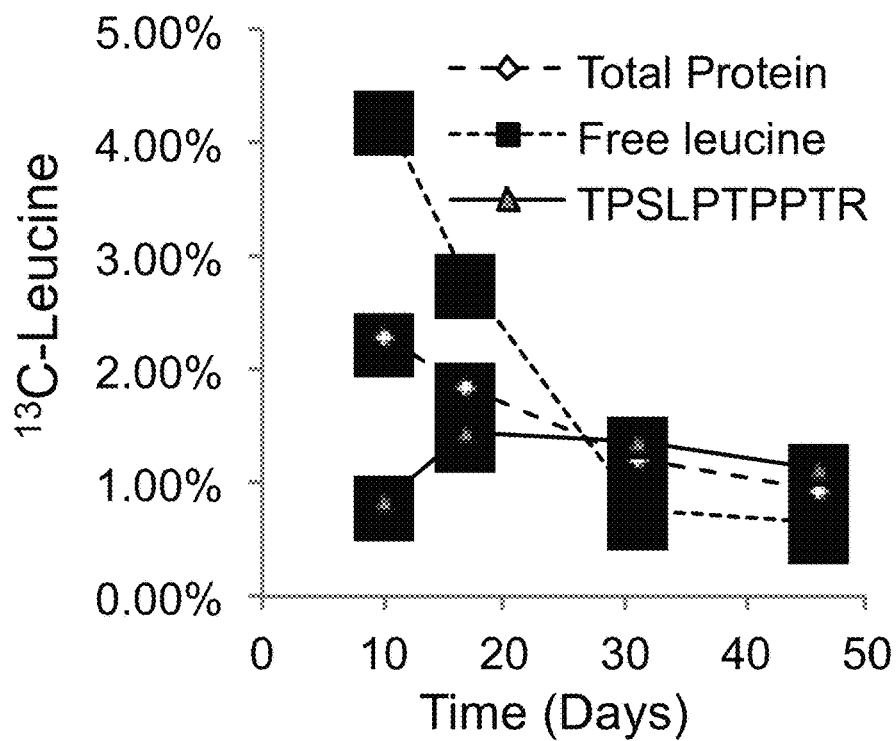
Figure 4E:
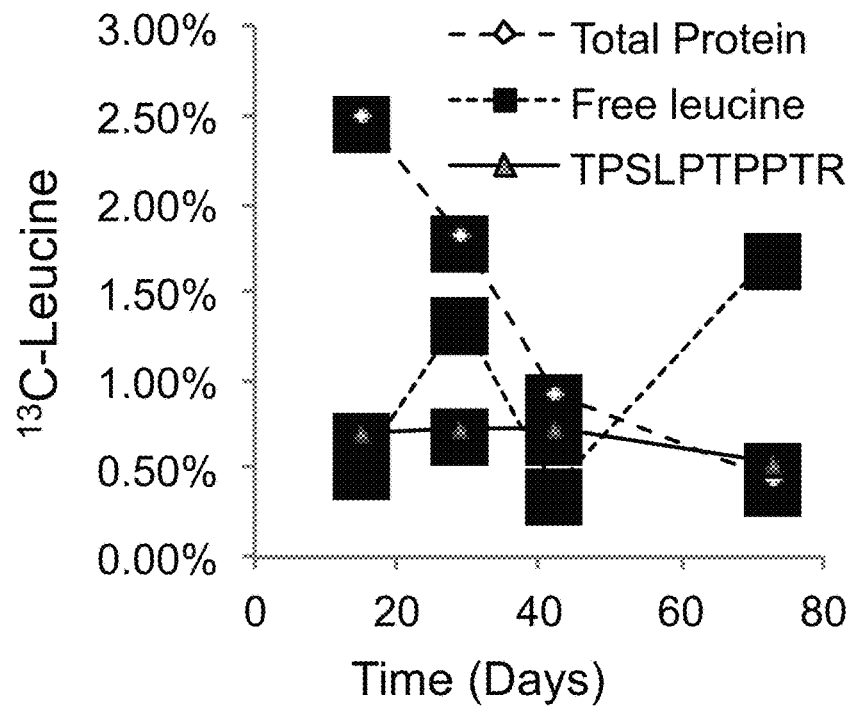
Figure 4F:
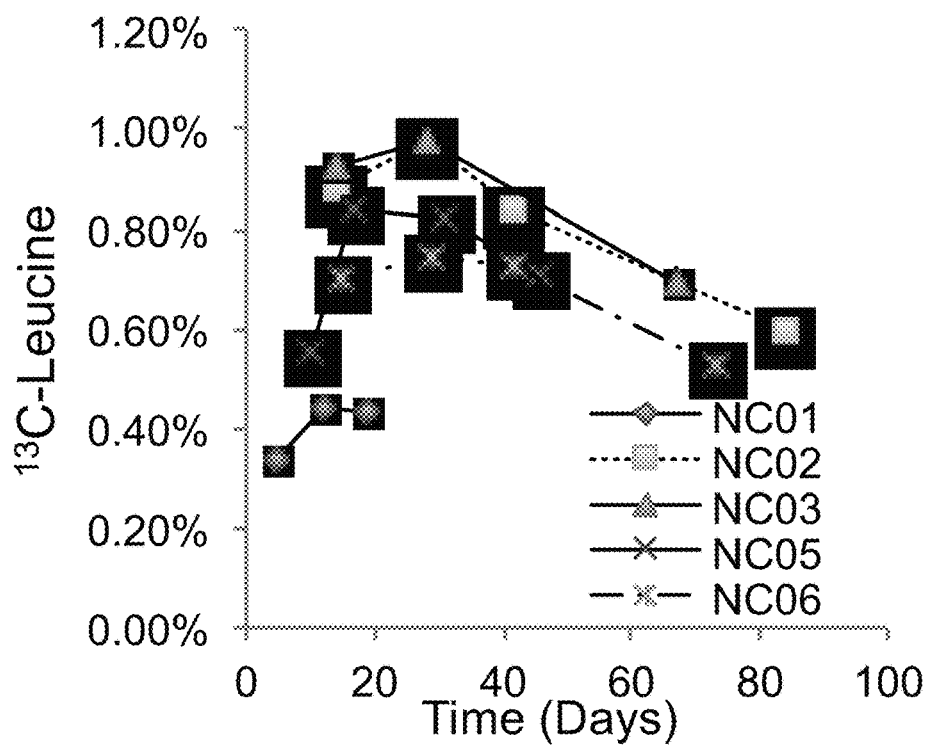

To generate a standard curve for TPSLPTPPTR peptide (SEQ ID NO: 2), HEK293T overexpressing tau were incubated with $^{13}C_6$-leucine labeled media for collection of labeled extracellular tau in the media. Briefly, HEK293T cells were labeled with $^{13}C_6$-leucine at 0%, 0.078%, 0.156%, 0.312%, 0.625%, 1.250%, and 2.5%, and labeled cell media was subjected to IP/MS methods described above. The standard curve demonstrates a linear correlation of predicted and measured percent labels and suggests that the limit of detection (LOQ) of TPSLPTPPTR peptide (SEQ ID NO: 2) is approximately 0.1% (FIG. 2C).

TABLE 1

| | 2N4R full length tau epitope |
|---|---|
| Tau12 | Amino acids 9-18 |
| HJ8.5 | Amino acids 27-35 |
| HJ8.7 | Amino acids 118-122 |
| Tau1 | Amino acids 194-198 |
| Tau5 | Amino acids 210-230 |
| HJ9.3 | Amino acids 306-321 |

TABLE 1-continued

| | 2N4R full length tau epitope |
|---|---|
| HJ9.1 | Amino acids 392-399 |
| Tau7 | Amino acids 430-441 |

Example 2. Stable Isotope Labeling Kinetics (SILK) of Tau In Vitro

Figure 1B:
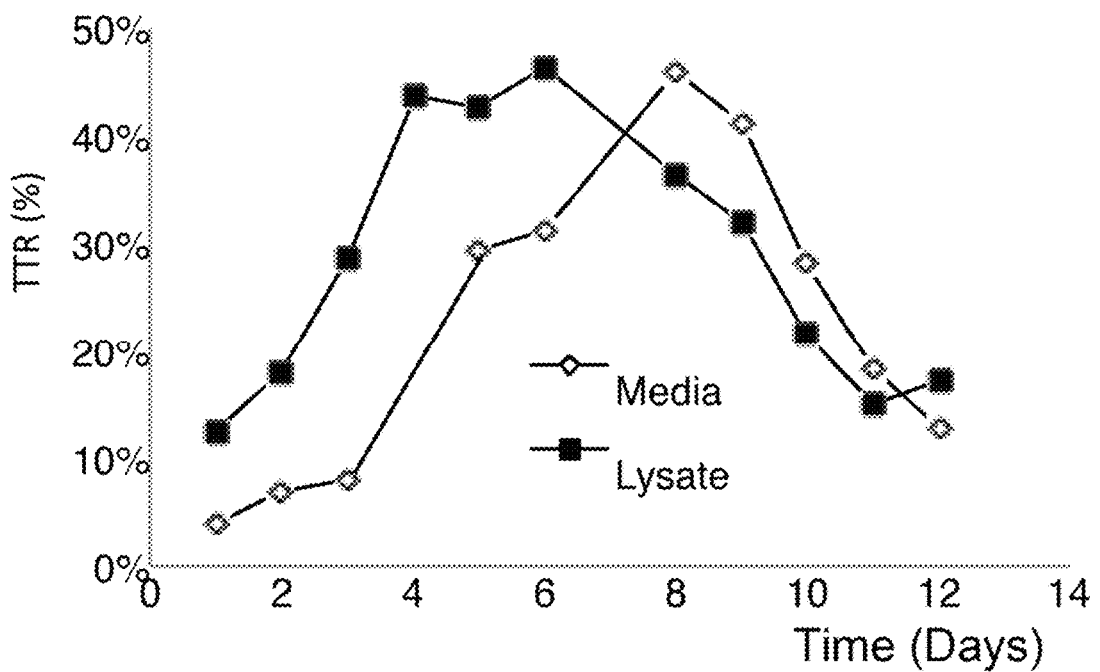

To test the feasibility of the Tau SILK method in vitro, two cell culture models were used for a proof of principle experiment. In the first model, SH-SY5Y human neuroblastoma cells were used, as these cells were previously shown to produce extracellular tau in the media. SH-SY5Y cells were cultured and labeled with 50% $^{13}C_6$-Leucine labeled media for 6 days followed by 6 days of unlabeling, and media and cell lysates were collected and subjected to IP/MS analyses for tau (FIG. 1A). Using TPSLPTPPTR (SEQ ID NO: 2) to quantify labeled tau, we observed a steady increase in labeling towards the 40-50% $^{13}C_6$-leucine precursor in the lysate and the media (FIG. 1B). A two to three day delay was observed before the detection of labeled tau in the media compared with the lysate, suggesting that it takes two to three days to release labeled tau from the lysate to the media. A steady decrease in labeling toward the baseline was also observed in the media and lysate after switching back to the $^{12}C_6$-leucine media. Based on 20-25% labeling (i.e. half of the labeled leucine precursor of 50% label) at day 2-3 (lysate) or 5-6 (media) on the production curve, we estimate that the half-life of extracellular tau in the lysate and media is approximately 3 days.

Figure 1C:
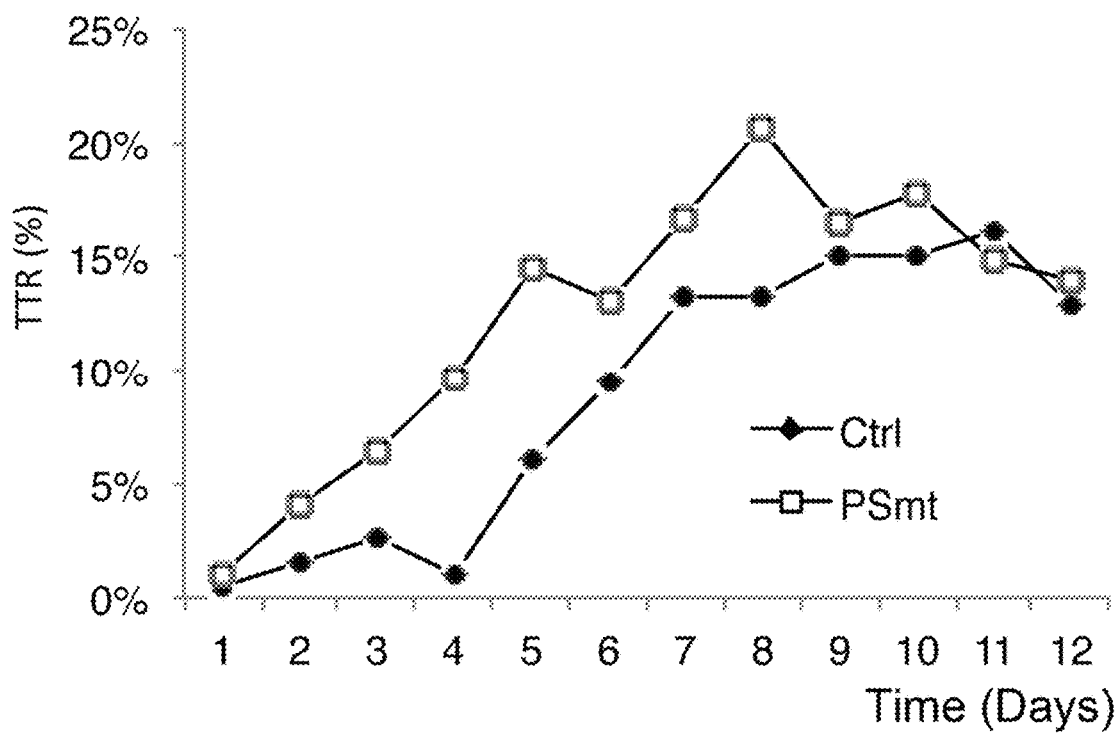

In the second model, induced pluripotent cells (iPSCs) obtained from skin fibroblasts of a Presenilin 1 mutant H163R (PSmt) carrier and a non-carrier (Ctrl) were used. These iPSCs were differentiated into neurons and subjected to Tau SILK method. iPSCs from AD patients have been previously reported to secrete increased tau in the media. In these experiments, iPSCs were subjected to 6 days of 50% $^{13}C_6$-leucine labeled media followed by 6 days of unlabeling (FIG. 1A). Only media was collected. Using TPSLPTPPTR (SEQ ID NO: 2) to quantify tau leucine labeling, we observed a steady increase in labeling towards the 20% $^{13}C_6$-leucine precursor in the media (FIG. 1C). 6 days were not sufficient to reach 50% labeling and the labeling continued to increase after switching back to regular media. The difference in the labeling curve between SH-SY5Y cells and iPSC neurons may be due to the fact that iPSCs are terminally differentiated cells while SH-SY5Y cells are dividing cells. Interestingly, PSmt had a steeper production curve, suggesting that the production of tau is increased in iPSC neuron of PSmt.

These in vitro proof of principle experiments demonstrate the quantitation of tau tryptic peptide, TPSLPTPPTR (SEQ ID NO: 2) using two cell culture models. Together, these results strongly suggest that a tau SILK study is feasible in humans.

Example 3. Stable Isotope Labeling Kinetics (SILK) of Tau in Humans

FIG. 3 shows an overview of one embodiment of the method. Briefly, normal control (NC) subjects (ages 32-73) were placed on a prepackaged low leucine diet and labeled with $^{13}C_6$-leucine for 5 (NC01) or 10 (NC02, NC03, NC05, NC06, NC07, NC08) days. $^{13}C_6$-leucine was administered to participants by dissolving 330 mg of the powder into Kool-Aid and drinking three times a day for a total soluble daily dose of 1 g. During the labeling period, overnight fasting blood draws were conducted on days 1 and 10 for the plasma leucine measurement. After labeling, participants resumed a normal diet. Lumbar punctures (LPs) and blood draws were performed approximately 14 days, 28 days, 42 days, and 67-84 days after labeling began (actual time points slightly differed between participants). 1 mL of each CSF sample is subjected to an immunoprecipitation/mass spectrometry (IP/MS) method to measure human tau. Briefly, tau is immunoprecipitated from the biological sample using a tau specific antibody and is then digested, resulting in multiple peptides that include leucine (FIG. 2). In particular, trypsin may be used for digestion and the peptide TPSLPT-PPTR (SEQ ID NO: 2) used for quantitation. Other enzymes and peptides may also be used.

To validate the tau SILK method in vivo, CSF samples were initially obtained from 5 normal control (NC) participants who were orally administered $^{13}C_6$ leucine for 5 (N001) or 10 days (NC02, NC03, NC05, NC06) days (FIG. 4). The half-life of tau in human CNS, for these subjects, is approximately 15 days. The exact measure of the half-life of tau has a range, i.e. about 10 to about 30 days. FIG. 5 includes data from two additional participants (i.e. NC07 and NC08). After inclusion of these two additional subjects, the half-life settled out to be approximately 19.6 days, with a range similar to the initial calculation (13-30 days, CV 32.2%).

account. For example, a monoexponential slope analysis, assumes that no tracer incorporation occurs in the product protein during the period of the slope analysis, i.e. the precursor pool (plasma leucine) contains no label. In a protein with a long half-life and long-term labeling, a compartmental model is necessary to account for the enrichment of the precursor pool as a function of time. The model begins with a 3×/day appearance of oral tracer into plasma over 10 days, and a whole-body plasma protein pool that accounts for the shape of the plasma leucine time course out to 84 days following tracer ingestion. Brain (including CSF) and plasma proteins derive tracer leucine from plasma, so the shape of the plasma leucine time course defines the time course for tracer availability for the formation of these proteins. The model consists of a series of compartments connected by first order rate constants k(i,j), which reflect the fraction of compartment j transported to compartment i per day.

With this tracer input time course defined, the shape of the SILK curve for each protein is uniquely determined by its fractional turnover rate (FTR) or irreversible loss. Results for one subject are shown in FIG. 6. Results for subjects NC02, NC03, NC04, NC05, NC06, NC07 and NC08 are shown in FIG. 7B-G, respectively. A summary of the participants' fractional turnover rate (FTR), half-life of CNS tau, and other information (age, weight, height, BMI, gender and demographic) is shown in Table 2, below.

TABLE 2

| Participant | FTR (pools/day) | Half-life (Days) | Age | Weight (kg) | Height (cm) | BMI | Gender | Demographic |
|---|---|---|---|---|---|---|---|---|
| NC02 | 0.0492 | 14.1 | 51 | 56.1 | 170.2 | 19.4 | male | AA |
| NC03 | 0.0532 | 13.0 | 66 | 82.2 | 180.0 | 25.4 | male | Cauc |
| NC05 | 0.0414 | 16.7 | 32 | 69.4 | 175.3 | 22.6 | male | Cauc |
| NC06 | 0.0275 | 25.2 | 72 | 95.6 | 172.3 | 32.2 | male | Cauc |
| NC07 | 0.0350 | 19.8 | 73 | 88.4 | 180.3 | 27.2 | male | AA |
| NC08 | 0.0240 | 28.9 | 60 | 72.1 | 152.4 | 31.0 | female | Cauc |
| Average | 0.0384 | 19.6 | 59.0 | 77.3 | 171.8 | 26.3 | | |
| Std Dev | 0.0117 | 6.3 | 15.5 | 14.3 | 10.3 | 4.9 | | |
| CV (%) | 30.4111 | 32.2 | 26.3 | 18.5 | 6.0 | 18.7 | | |

Figure 5A:
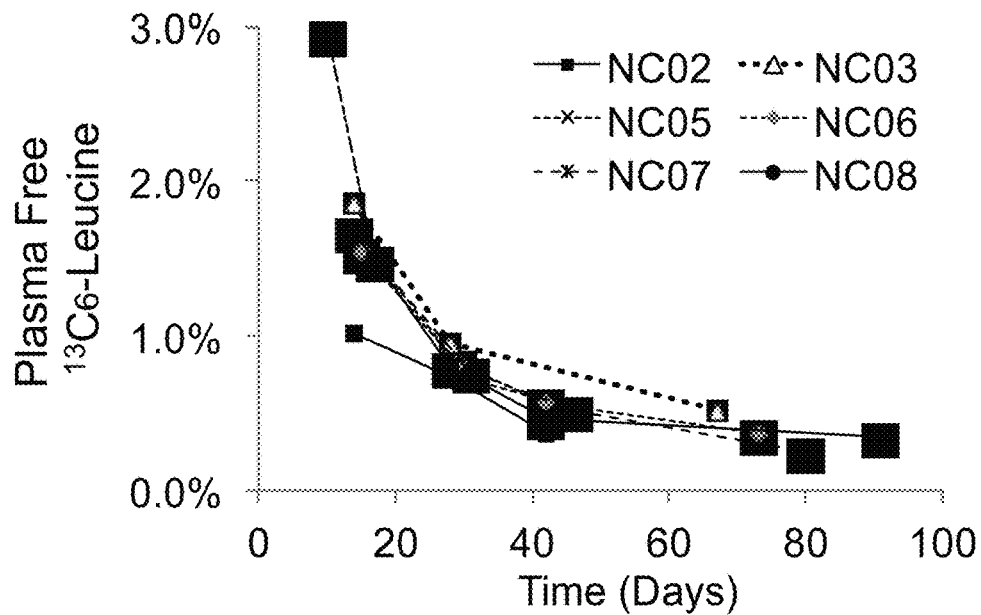
FIG. 5A-B depicts graphs showing tau SILK analyses for six participants (i.e. NC02, NC03, NC05, NC06, NC07, and NC08) who were orally labeled for 10 days with $^{13}C_6$-leucine, and from whom CSF samples were obtained. (A) free leucine in the plasma measured by gas chromatography (GC)-MS, and (B) $^{13}C_6$ Leucine labeled tau in CSF measured in triplicates using liquid chromatography LC/MS.
Figure 5B:
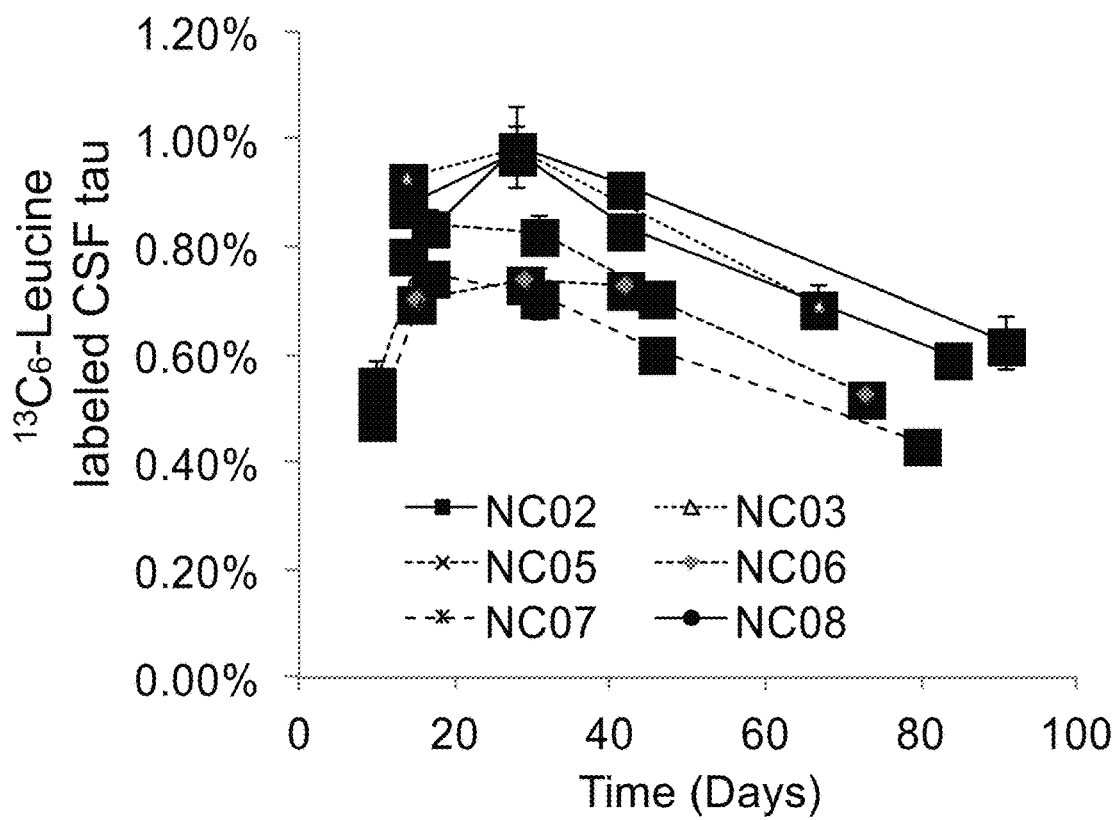
Figure 6A:
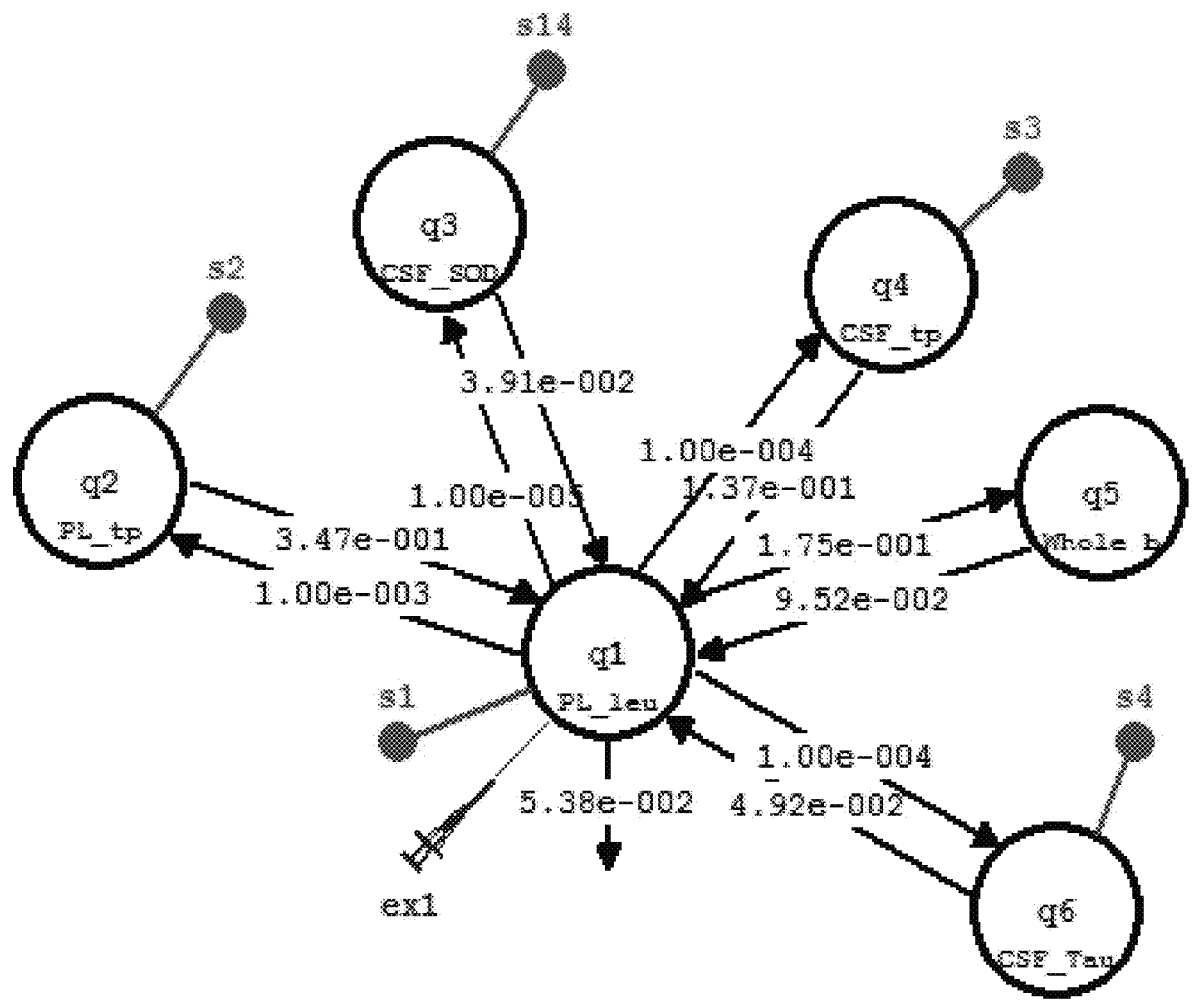
FIG. 6A-D depicts an illustration and graphs showing one embodiment of a compartmental model of tau SILK for one subject. (A) Schematic diagram illustrating a compartmental model that accounts for plasma leucine, CSF tau, CSF total protein, and plasma total protein tracer labeling kinetics. SOD1, another slow turnover protein whose kinetics were measured in the samples were also included in the model for a comparison. The model comprises a series of compartments connected by first order rate constants, k, which reflect the fraction of compartment j transported to compartment i per day. (B) Plasma leucine tracer labeling kinetics. The model begins with a 3x/day appearance of oral tracer into plasma over 10 days, and a whole-body plasma protein pool that accounts for the shape of the plasma leucine time course out to 84 days following tracer ingestion. Brain (including CSF) and plasma proteins derive tracer leucine from plasma. Therefore, the shape of the plasma leucine time course defines the time course for tracer availability for the formation of these proteins. (C) CSF Tau and SOD1 tracer labeling kinetics. The shape of the SILK curve for each protein is uniquely determined by its fractional turnover rate (FTR). The FTRs for tau and SOD1 are 0.049 and 0.039 pools/day, respectively. (D) CSF total protein and plasma total protein tracer labeling kinetics.
Figure 6B:
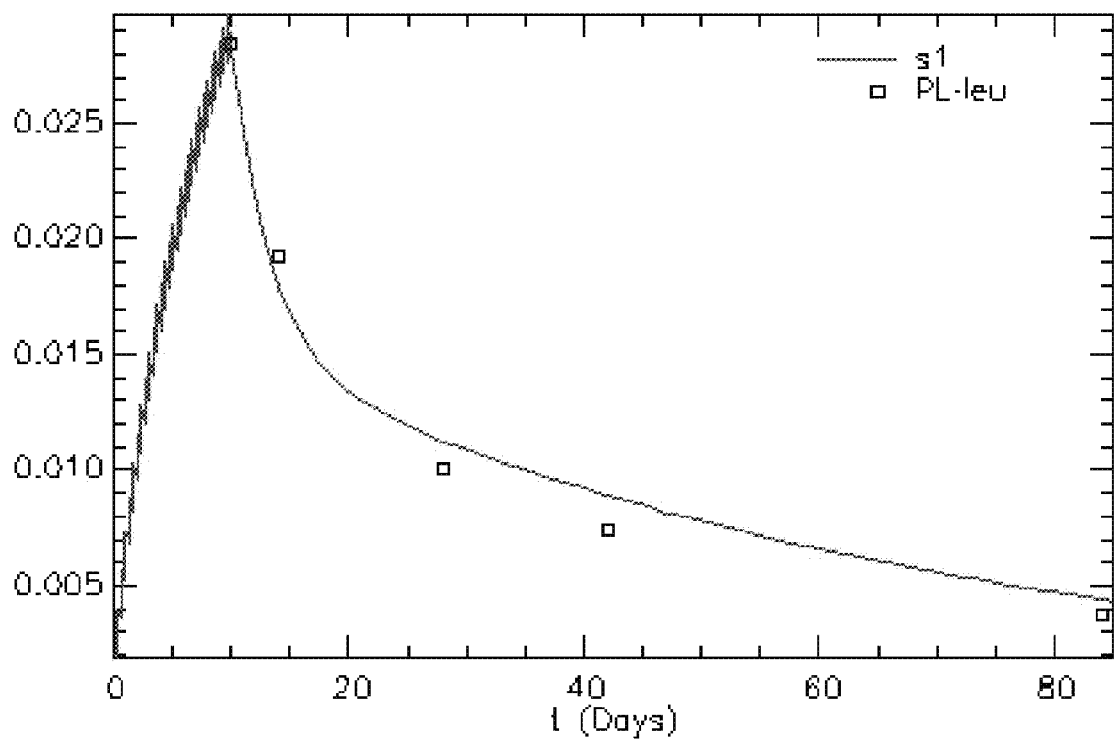
Figure 6C:
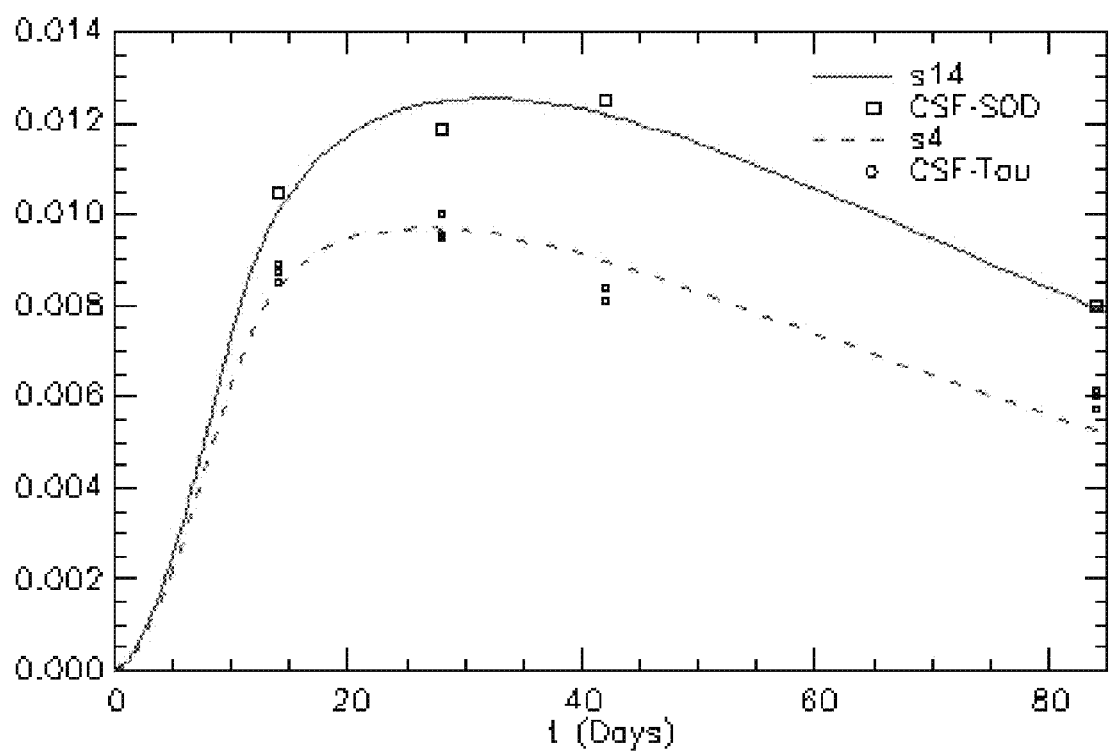
Figure 6D:
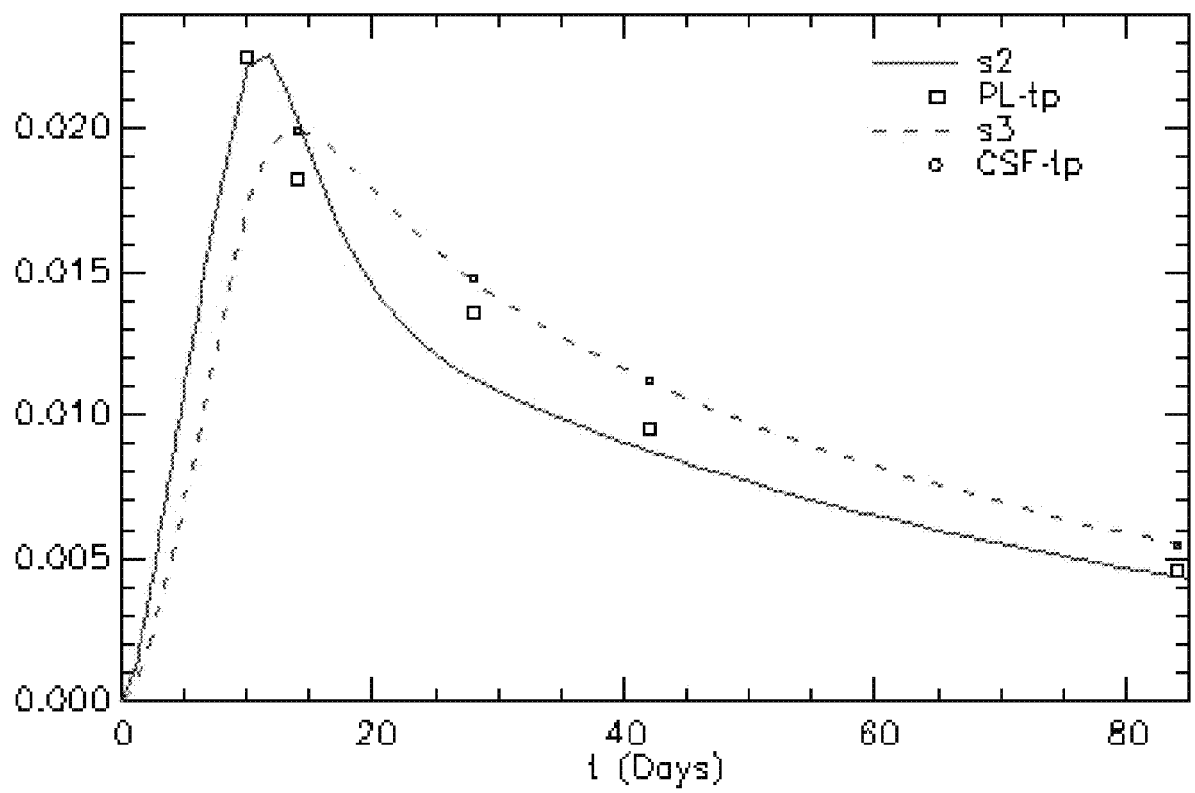
Figure 7A:
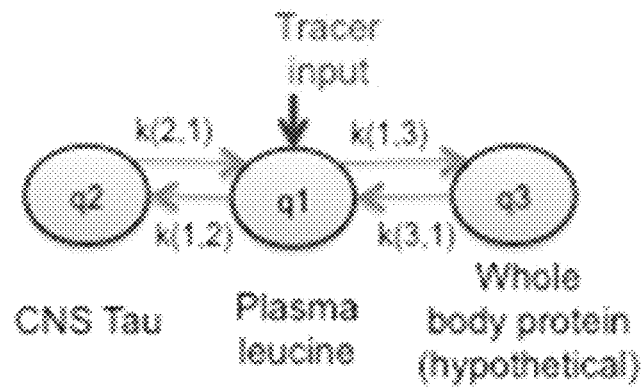
FIG. 7A-G depicts an illustration and graphs showing one embodiment of a compartment modeling of $^{13}C_6$ oral labeling of tau. (A) The model consists of a series of compartments (q1-q3) connected by first order rate constants k(i,j), which reflect the fraction of compartment j transported to compartment i per day. The model fits to the labeling of plasma free leucine (green) and CNS tau (red) of all the participants. Y axis: Free $^{13}$C-Leucine and $^{13}$C-Leucine labeled CSF tau. X axis: Time (Days). Models of NC02 (B), NC03 (C), NC05 (D), NC06 (E), NC07 (F), and NC08 (G) are shown.
Figure 7B:
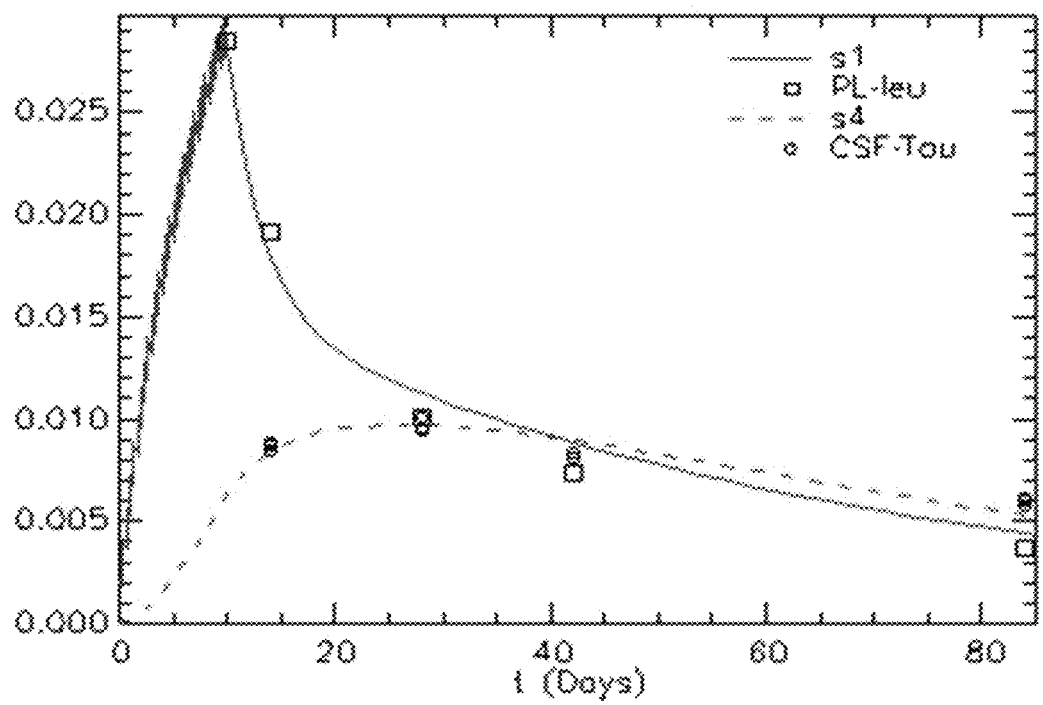
Figure 7C:
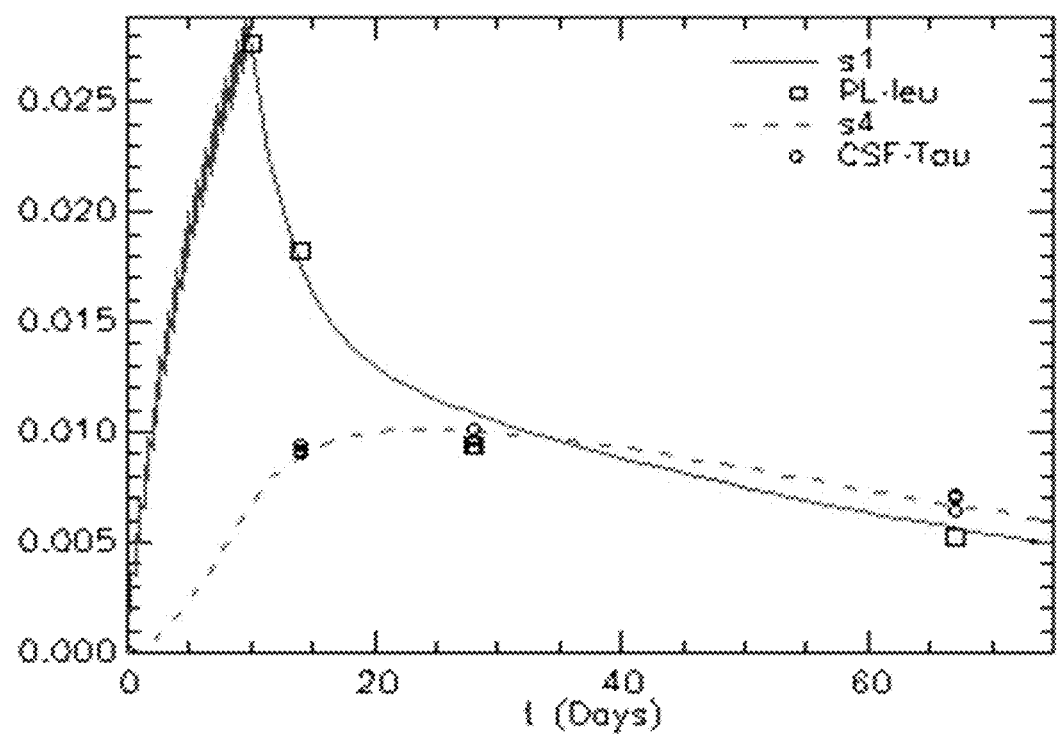
Figure 7D:
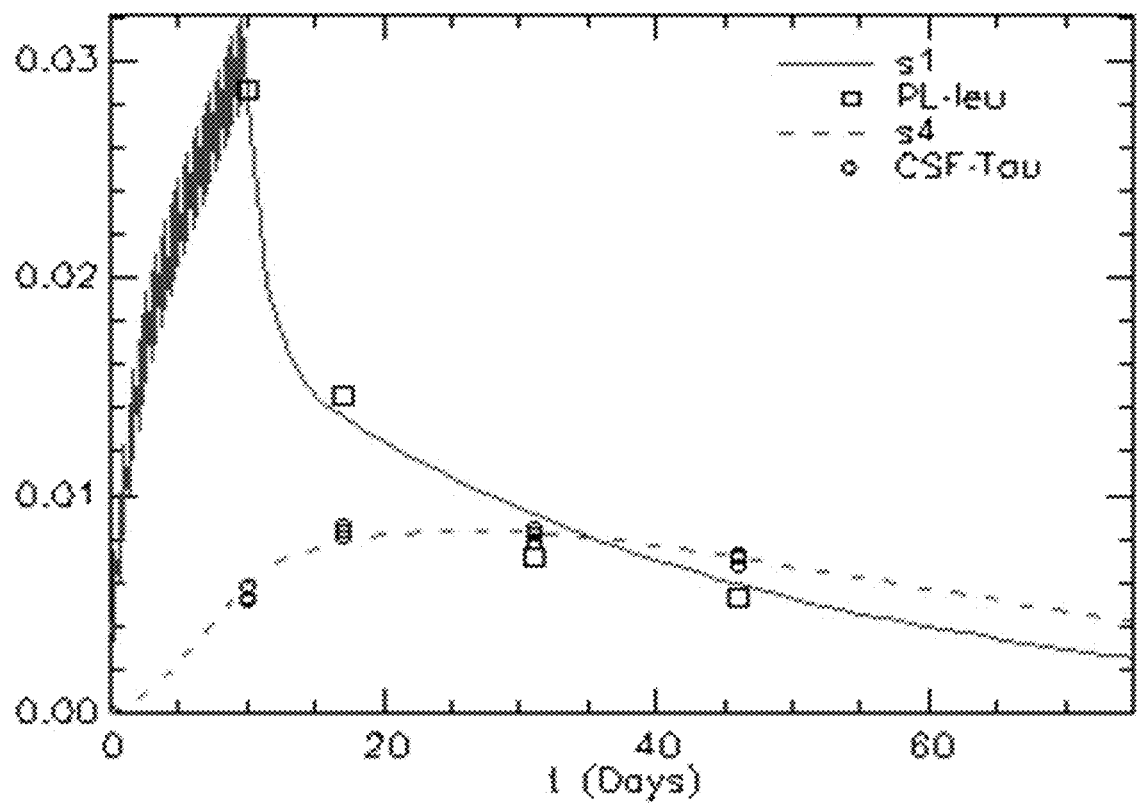
Figure 7E:
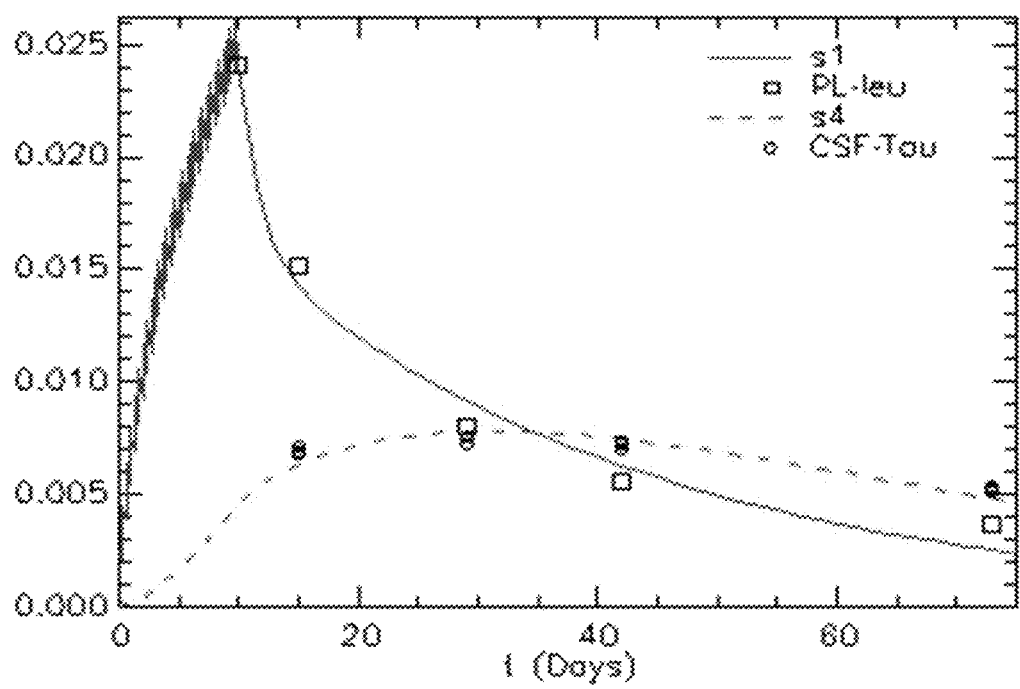
Figure 7F:
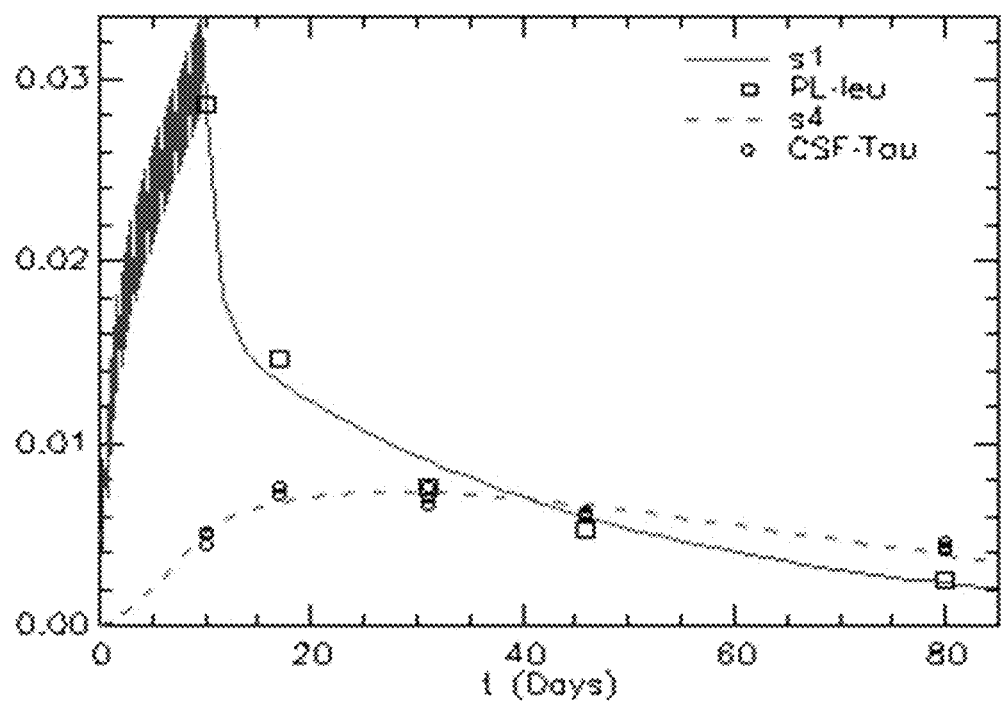
Figure 7G:
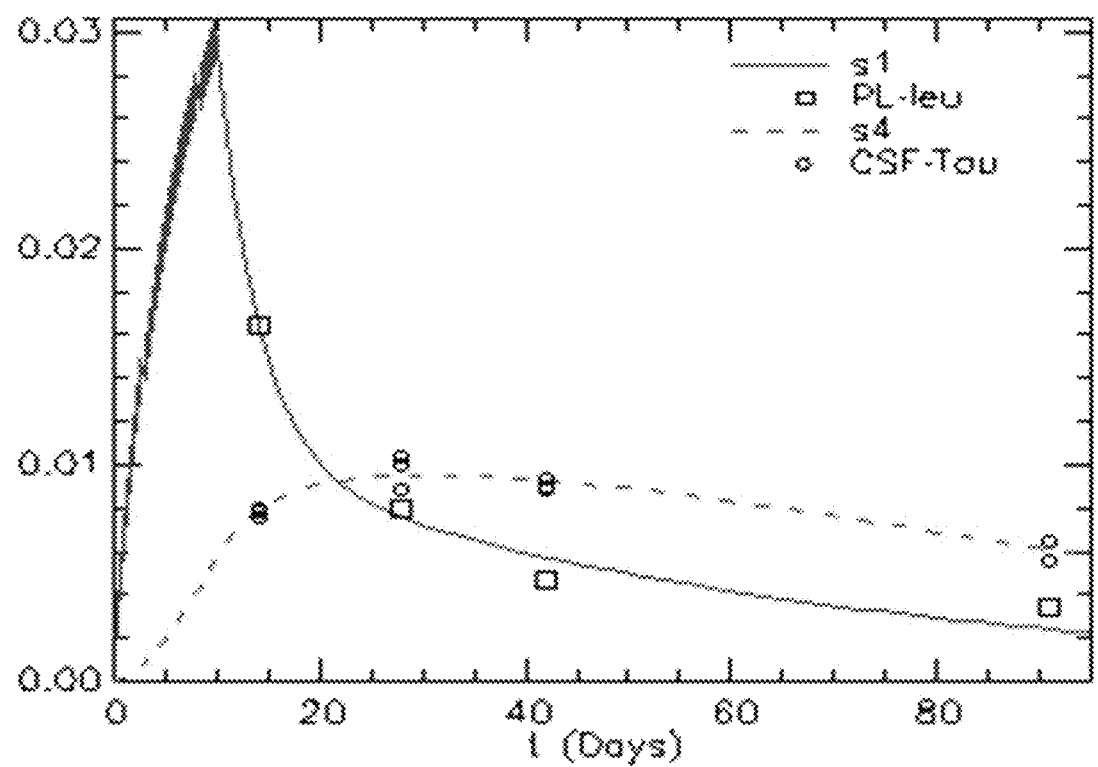

The tau kinetic curves in FIG. 4 and FIG. 5 collectively show that tau turnover is slower than the total protein. With 10 days of oral labeling, robust labeling of $^{13}C_6$-leucine (free amino acid pool) could be achieved in plasma (2-3%), indicating that the tracer concentrations reached sufficient levels during a controlled leucine diet (FIG. 5A). The CNS tau labeling curves displayed a slow rise (10-30 days) and fall (+80 days), indicating a slow turnover rate of CNS tau (FIG. 5B).

Example 4. Tau Kinetic Model

To obtain a full kinetic curve from the limited number of measured time points and to calculate the half-life of tau, a compartmental model that that accounts for plasma leucine, CSF Tau, CSF total protein, and plasma total protein tracer labeling kinetics has been developed (10 d of 1 g/day oral $^{13}C_6$-leucine). SOD1, another slow turnover protein whose kinetics were measured in the same samples were also included in the model for a comparison. A comprehensive model that accounts for multiple sights of data collection is preferable to previously utilized "model-independent" methods of assessing turnover kinetics, because it takes the shape of the precursor (i.e. plasma leucine) time course into Methods for the Examples.

Preparation of $^{13}C_6$-Leucine Labeled Tau Standard Curve:

Labeled media standard was prepared by labeling full-length (FL. 2N4R) tau transiently overexpressed in HEK293T cells. HEK293T cells were grown in Dulbecco's Modified Eagle Media (DMEM, Sigma, D5546) supplemented with 10% fetal bovine serum (Sigma, F6178), and split into 6-well plates the day before transfection. On the day of the transfection, the media was spiked with $^{13}C_6$-leucine (Cambridge Isotopes, CLM-2262) into DMEM containing 1.05 g/L of $^{12}C_6$-leucine to the final tracer to trace ratio (TTR) of 2.5%, 1.25%, 0.625%, 0.312%, 0.156%, 0.078% and 0%. HEK293T were transiently transfected with FLtau-pcDNA3.1 using Fugene HD (Promega, E2312). Media and cells were harvested after 6 days. Media were spun at 15K g for 5 min and the supernatant was diluted to match the signal obtained from human CSF tau, aliquoted, and then frozen at −80° C. Cells were washed once with PBS, collected in cold PBS with protease inhibitor cocktail (Roche, 04693116001), spun at 15K g for 5 minutes, then the aliquots were frozen at −80° C.

Isolation and Mass Spectrometric Analysis of $^{13}C_6$-Leucine Labeled Tau and Plasma Free $^{13}C_6$-Leucine:

CNBr-activated Sepharose beads (GE Healthcare 17-0430-01) were crosslinked to Tau12, Tau1, Tau5 antibody (mouse monoclonal, provided by Drs. Skip Binder and Nick Kanaan at Michigan State University), HJ8.5, HJ8.7, HJ9.3, HJ9.1 (mouse monoclonal, provided by Dr. David Holtzman and Hong Jiang) at a concentration of 3 mg antibody per g of beads. Soluble tau was immunoprecipitated from 1 mL of human CSF from a participant, human CSF collected from the Barnes-Jewish Hospital Neurology Critical Care Unit (St. Louis, Mo.) and cell culture media (SH-SYSY human neuroblastoma and HEK293T cells transiently overexpressing full-length tau) in detergent (1% NP-40), chaotropic reagent (5 mM guanidine), and protease inhibitors (Roche Complete Protease Inhibitor Cocktail). 30 uL of 50% slurry of the tau antibody beads were rotated with the solution for 90 minutes at room temperature. The beads were washed one time in 0.5M guanidine and two times in 25 mM triethyl ammonium bicarbonate buffer (TEABC, Fluka 17902). The bound tau was digested on-beads with 400 ng mass spectrometry grade trypsin (Promega, V5111) for 16 hours at 37° C. Tryptic digests were loaded on to TopTip C18 (Glygen, TT2C18.96), desalted, cleaned up and eluted per manufacturer's instructions. The eluted peptides solution was dried by vacuum centrifuge (CentriVap Concentrator Labconco) and were resuspended in 25 uL of a solution of 2% acetonitrile and 0.1% formic acid in MS grade water. A 5 uL aliquot of the peptide resuspension was subjected to nano-Acquity LC and MS analysis. The nano-Acquity LC (Waters Corporation, Milford, Mass.) was fitted with HSS T3 130C18 100□m×100 mm column and a flow rate of 0.5 □l/min of a gradient of solution A and B was used to separate the peptides. Solution A composed of 0.1% formic acid in MS grade water and solution B was 0.1% formic acid in acetonitrile. Peptides were eluted from the column with a gradient of 2% to 20% of solution B in 8 minutes, then 20% to 40% solution B for another 3 minutes before ramping up to 85% solution B in another 3 minutes to clean up the column. The Orbitrap Fusion was equipped with a nanoflex electrospray source (Thermo Scientific, San Jose, Calif.) Peptide ions sprayed into the ion-source were targeted and isolated in the quadrupole which were then fragmented by HCD and detected in the Orbitrap at a resolution of 60,000. The labeled tau peptide co-eluted with the unlabeled peptide and both were sequentially fragmented. The area under their chromatographic peak profiles were calculated and expressed as an area ratio.

To determine the percent enrichment of precursor $^{13}C_6$-leucine in the plasma at each time point, plasma proteins were precipitated with 10% trichloroacetic acid overnight at 4° C., then removed by spinning at 21,000×g for 10 minutes. The free amino acids in the supernatant were converted to N-heptafluorobutyryl n-propyl ester derivatives and isotopic enrichment for $^{13}C_6$-leucine [mass/charge ratio (m/z) 349 and 355] was analyzed via gas chromatography (GC)-negative chemical ionization-MS (Agilent 6890N Gas Chromatograph and Agilent 5973N Mass Selective Detector) as described previously[23]. Measurements of $^{13}C_6$-leucine incorporation into total protein was determined by subjecting 50 μL of tissue lysate to 10% TCA precipitation overnight at 4° C., centrifuging the samples at 21,000×g for 10 minutes, removing the supernatant, and sonicating the pellet in a cold 10% TCA solution, twice. The pellets were then subjected to acid hydrolysis in 6 N HCl for 24 hours at 110° C. Cation-exchange chromatography (50W-X8 resin) was then used to isolate the resultant amino acids with 6N $NH_4OH$ as the elution buffer. The samples were then dried on a speed-vacuum and processed for GC-MS. To account for the bias in tracer:tracee ratios (TTRs) that occurred as tracer enrichment increases, TTRs were converted to mole fraction labels (MFLs) by using the equation: MFL=(TTR)/(1+TTR).

Human Subjects:

Studies involving human subjects were approved by the Washington University Human Studies Committee and the General Clinical Research Center (GCRC). Informed consent was obtained from all participants. Participants underwent an initial screening visit that consisted of a physical and neurological examination. Exclusion criteria included evidence of neurologic disorder by history or examination, inability to safely take food and drink by mouth, lab values greater than twice normal, special diets (e.g. gluten-free), pregnancy, allergy to lidocaine, history of bleeding disorders, or contraindications for lumbar puncture. Participants were then placed on a prepackaged low leucine diet and labeled with $^{13}C_6$-leucine for 10 days. The low leucine diet (about 2000 mg leucine/day) was prepared by dieticians in the Washington University Research Kitchen, handed to the participants, then consumed at home. Food intake was monitored by a self-reported food journal. The $^{13}C_6$-labeled leucine, obtained from Cambridge Isotope Laboratories (CLM-2262), was administered to participants by dissolving 330 mg of the powder into 120 mL of Kool-Aid. Participants drank this $^{13}C_6$-leucine three times a day for a total soluble daily dose of 1 g. During the labeling period, overnight fasting blood draws were conducted on days 1 and 10. After labeling, participants resumed a normal diet. Lumbar punctures and blood draws were performed approximately 14 days, 28 days, 42 days, and 67-84 days after labeling began (actual time points differed slightly between participants).

Blood was centrifuged at 1800×g for 10 minutes and the supernatant (serum), aliquoted into low-binding 1.5 mL tubes, frozen on dry ice, and stored at −80° C. CSF was spun at 1000×g for 10 minutes at 4° C. and 1 mL aliquots were placed into low-binding 1.5 mL tubes, frozen on dry ice, and stored at −80° C.

Compartmental Modeling of Kinetic Data:

Modeling was conducted using the SAAM II software (Resource for Kinetic Analysis, University of Washington, Seattle) as described previously[23]. This model consists of a series of compartments connected by first order rate constants k(i,j), which reflect the fraction of compartment j transported to compartment i per day. The kinetic data for plasma free $^{13}C_6$-leucine were incorporated into a compartmental model as described in FIG. 4. The TPSLPTPPTR peptide was used for modeling as it had the most robust LC-MS signal.

What is claimed is:

1. An in vitro method for measuring the metabolism of soluble cerebral spinal fluid (CSF) tau in a subject, the method comprising:
   (a) administering at least one labeled amino acid to the subject on one or more days;
   (b) collecting at least one CSF sample from the subject between day 5 and about day 20, about day 20 and about day 40, about day 40 and about day 100, or a combination thereof;
   (c) separating a tau fragment from at least one CSF sample collected in step (b) using an antibody that has affinity within tau's N-terminus or mid-domain;
   (d) detecting and measuring by mass spectrometry the amount of labeled tau fragment, or the amount of labeled and unlabeled tau fragment, in at least one sample from step (c); and
   (e) calculating the metabolism of soluble CSF tau using the measurements from step (d), wherein the amount of labeled tau fragment in the sample at a given time reflects the metabolism of soluble CSF tau.

2. The method of claim 1, the method further comprising calculating a metabolic parameter of tau metabolism using the amounts of labeled and/or unlabeled tau determined in claim 1 step (c), the metabolic parameter selected from the group consisting of relative labeling, fractional synthesis rate, fractional clearance rate, absolute synthesis rate, absolute clearance rate, fractional turnover rate, lag time, half-life, peak time, and peak height.

3. An in vitro method for measuring the metabolism of soluble cerebral spinal fluid (CSF) tau in a subject, the method comprising:
   (a) separating a tau fragment from at least one CSF sample obtained from a subject, using an antibody that has affinity within tau's N-terminus or mid-domain;
   (b) detecting and measuring by mass spectrometry the amount of labeled tau, or the amount of labeled and unlabeled tau, in at least one sample from step (a); and
   (b) calculating the metabolism of soluble CSF tau using the measurements from step (b), wherein the amount of labeled tau in the biological sample at a given time reflects the metabolism of soluble CSF tau; and
   wherein
      (i) the label was administered on one or more days to the subject as one or more labeled amino acids, and
      (ii) at least one CSF sample was collected from the subject between day 5 and about day 20, day 20 and day 40, day 40 and day 100, or a combination thereof.

4. The method of claim 3, wherein the labeled amino acid was administered on two or more days between day 0 and about day 3.

5. The method of claim 3, wherein the labeled amino acid was administered on two or more days between day 0 and about day 5.

6. The method of claim 3, wherein the labeled amino acid was administered on two or more days between day 0 and about day 10.

7. The method of claim 3, wherein the labeled amino acid was administered daily.

8. The method of claim 3, wherein the label is administered to produce an amount of labeled amino acid in the CSF sample selected from the group consisting of about 0.1%, about 0.2%, about 0.5%, about 1%, about 2%, about 5%, about 0.1 to about 20%, and about 0.1 to about 10%.

9. The method of claim 3, wherein the subject is a rodent.

10. The method of claim 3, wherein the subject is a human.

11. The method of claim 3, wherein the tau fragment is separated by immunoprecipitation.

12. The method of claim 3, the method further comprising calculating a metabolic parameter of soluble tau metabolism using the amounts of labeled and/or unlabeled tau determined in step (b), the metabolic parameter selected from the group consisting of relative labeling, fractional synthesis rate, fractional clearance rate, absolute synthesis rate, absolute clearance rate, fractional turnover rate, lag time, half-life, peak time, and peak height.

13. The method of claim 3, wherein tau is a phosphorylated tau isoform.

14. The method of claim 3, wherein at least one CSF sample is collected from the subject between about day 20 and about day 40, about day 40 and about day 100, or a combination thereof.

15. The method of claim 3, wherein the labeled amino acid is labeled with a non-radioactive isotope.

16. The method of claim 15, wherein the non-radioactive isotope is selected from the group consisting of $^{2}H$, $^{13}C$, $^{15}N$, $^{17}O$, $^{18}O$, $^{33}S$, $^{34}S$, and $^{36}S$.

17. The method of claim 16, wherein the labeled amino acid is $^{13}C_6$ leucine.

18. The method of claim 3, wherein the labeled amino acid was administered to the subject intravenously or orally.

19. The method of claim 18, wherein the labeled amino acid was administered to the subject orally, at a total daily dose of about 0.1 g to about 10 g, on two or more days between day 0 and about day 10.

* * * * *

UNITED STATES PATENT AND TRADEMARK OFFICE
CERTIFICATE OF CORRECTION

| | |
|---|---|
| PATENT NO. | : 10,830,775 B2 |
| APPLICATION NO. | : 15/515909 |
| DATED | : November 10, 2020 |
| INVENTOR(S) | : Bateman et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 41 days.

Signed and Sealed this
Fourteenth Day of February, 2023

Katherine Kelly Vidal
*Director of the United States Patent and Trademark Office*